United States Patent
Moritoki et al.

[11] Patent Number: 5,654,343
[45] Date of Patent: Aug. 5, 1997

[54] METHOD OF TREATING A NITRIC OXIDE-ASSOCIATED DISEASE WITH PHENANTHRENE DERIVATIVES

[75] Inventors: Hideki Moritoki; Yoshihisa Takaishi, both of Tokushima; Masakazu Adachi, Takasaki; Yukihisa Ono, Tokushima-ken, all of Japan

[73] Assignee: Otsuka Pharmaceutical Co., Ltd., Tokyo, Japan

[21] Appl. No.: 495,645

[22] PCT Filed: Oct. 11, 1994

[86] PCT No.: PCT/JP94/01695

§ 371 Date: Jun. 6, 1995

§ 102(e) Date: Jun. 6, 1995

[87] PCT Pub. No.: WO95/10266

PCT Pub. Date: Apr. 20, 1995

[30] Foreign Application Priority Data

Oct. 13, 1993 [JP] Japan .................... 5-255944
May 6, 1994 [JP] Japan .................... 6-094559

[51] Int. Cl.$^6$ .................... A61K 31/135; A61K 31/03; A61K 31/01
[52] U.S. Cl. .................... 514/654; 514/751; 514/754; 514/762; 514/921
[58] Field of Search .................... 514/751, 754, 514/762, 921, 654

[56] References Cited

U.S. PATENT DOCUMENTS 5,192,817  3/1993  Takaishi et al. .................... 549/298
5,385,947  1/1995  Godel et al. .................... 514/654

FOREIGN PATENT DOCUMENTS

A4211035  8/1992  Japan.
A61746    1/1994  Japan.
A6192155  7/1994  Japan.
A6263688  9/1994  Japan.

Primary Examiner—Kevin E. Weddington
Attorney, Agent, or Firm—Sughrue, Mion, Zinn, Macpeak & Seas

[57] ABSTRACT

This invention provides a nitric oxide synthesis inhibitor composition comprising, as an active ingredient, at least one member of the group consisting of various phenanthrene derivatives, typically represented by the following general formula (1), and salts thereof.

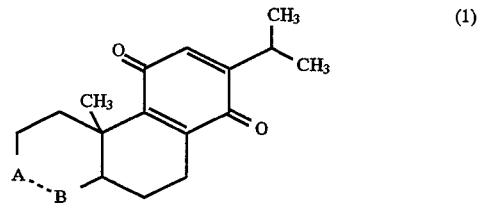

The nitric oxide synthesis inhibitor composition of this invention is useful for the prophylaxis and therapy of nitric oxide-associated diseases such as endotoxin shock.

6 Claims, No Drawings

METHOD OF TREATING A NITRIC OXIDE-ASSOCIATED DISEASE WITH PHENANTHRENE DERIVATIVES

TECHNICAL FIELD

This application is a 371 of PCT/JP94/01695 filed Oct. 11, 1994.

This invention relates to a nitric oxide synthesis inhibitor which is of use as a medicament.

BACKGROUND ART

Resent research has clarified that nitric oxide (NO) is the very vascular endothelium-derived relaxing factor (EDRF) and that it is functioning as a chemical transmitter or modulator not only in vascular endothelial cells but also in such other cells or tissues as the brain, platelet, macrophage, neutrophil, and non-adrenergic, non-cholinergic nervous systems. This nitric oxide is produced by NO synthase using L-arginine (L-Arg) as the substrate. It has been reported that said NO synthase has at least two iso-forms. One is a constitutive-type enzyme which occurs in the vascular endothelium and the brain. The other is an inducible type-enzyme which occurs in the macrophage and vascular smooth muscle. Meanwhile, it is known that the above inducible-type NO synthase is induced by a variety of cytokines such as interleukins (ILs), interferon-γ (IFN-γ), tumor necrosis factor (TNF), etc., or by endotoxins and a broad spectrum of cytokines derived from endotoxins.

It has also been reported that in the event an excess of said nitric oxide is produced and released in the body, various cells and tissues are injured not only by its inherent blood vessel-relaxing effect but also by the chemical reactivity of nitric oxide itself. In particular, it is known that the above-mentioned inducible NO synthase, which is known to be induced by endotoxins and various cytokines, is deeply associated, through the nitric oxide it produces, with the onset and morbidity of endotoxin shock and bleeding tendency. The inducible NO synthase attracts attention in connection with its relation to such morbidity, rather than the physiological roles it plays.

Meanwhile, a variety of inhibitor substances that inhibit synthesis of said nitric oxide are also known and the inhibitors which are most widely used today are various L-arginine derivatives having a methyl or nitro group in the ω-position (guanidino group) of L-arginine (L-Arg), which are reversible or irreversible competitive inhibitors of NO synthase for the L-Arg substrate.

Refer to the following reference documents regarding the prior mentioned above for more information.

(1) Hideki Moritoki: Blood Vessel and Endothelium, Vol. 2, No. 4 p. 32–40, 1992
(2) Takaaki Akaike et al.: Advances in Medicine, Vol. 166, No. 3, p. 161–164, 1993, 7, 17
(3) Hideki Moritoki, et al., Br. J. Pharmacol., (1991), 102, 841–846
(4) Hideki Moritoki, et al., Br. J. Pharmacol., (1992), 107, 361–366

DISCLOSURE OF INVENTION

With the object of providing a nitric oxide synthesis inhibitor substance or composition as a medicine which would take the place of the hitherto-known NO synthase inhibitors mentioned above, the inventors of this invention carried out intensive research, and found that a series of phenanthrene derivatives and salts thereof which they previously developed as substances having interleukin-1 (IL-1) inhibitory activity (JP Kokai H4-211035) possess nitric oxide synthesis inhibitory activity meeting the above object. The invention has been accomplished based on these findings.

This invention, therefore, is directed to a nitric oxide synthesis inhibitor comprising at least one phenanthrene derivative selected from the group consisting of the compounds of the following formulas (1)–(12), or a salt thereof, as an active ingredient.

General formula (1):

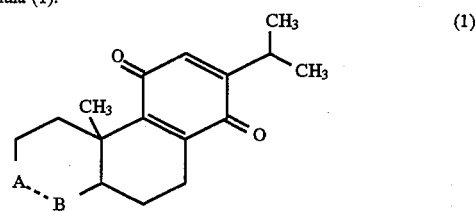

wherein the group —A...B— represents

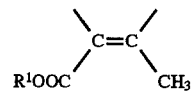

($R^1$ represents hydrogen or lower alkyl),

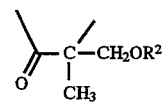

($R^2$ represents hydrogen or lower alkanoyl),

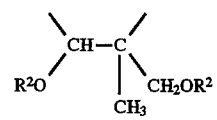

($R^2$ is as defined above), or

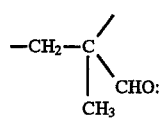

Formula (2):

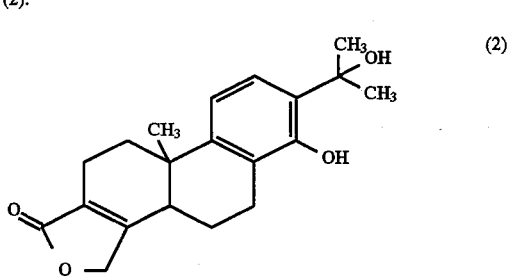

Formula (3):

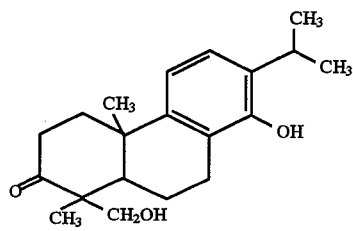

General formula (4):

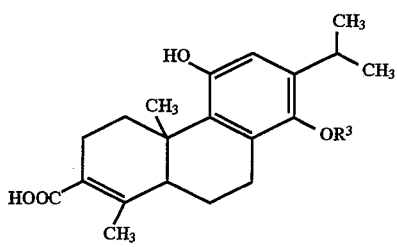

wherein $R^3$ represents hydrogen or methyl

Formula (5):

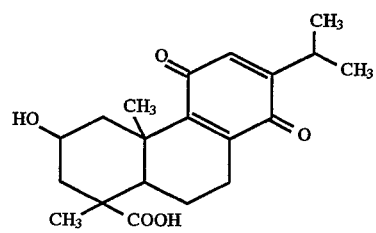

General formula (6):

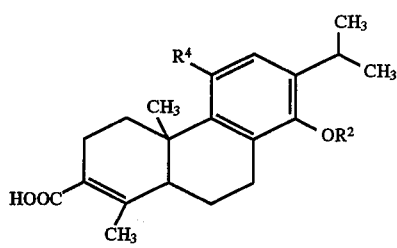

wherein $R^4$ represents lower alkanoyloxy; $R^2$ is as defined above

General formula (7):

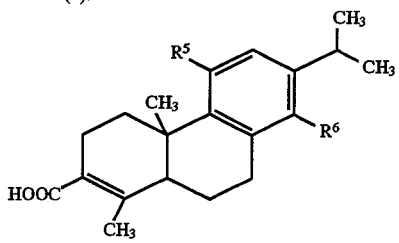

wherein $R^5$ and $R^6$ each represent lower alkoxy

General formula (8):

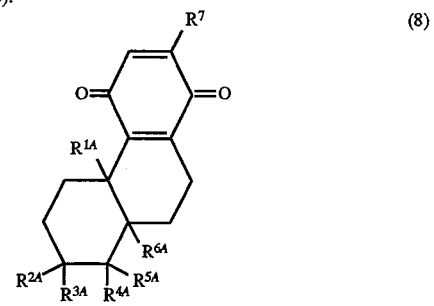

wherein $R^{1A}$ represents lower alkyl; $R^{2A}$ represents formyl; $R^{3A}$ represents hydroxy; or $R^{2A}$ and $R^{3A}$, taken together, represent oxo; and $R^{3A}$ may form a double bond in combination with $R^{5A}$ which is defined below; $R^{4A}$ represents lower alkyl; $R^{5A}$ represents hydrogen or hydroxy(lower)alkyl or may form a double bond in combination with $R^{3A}$ or $R^{6A}$ which is defined below; $R^{6A}$ represents hydrogen or may form a double bond in combination with $R^{5A}$; $R^7$ represents hydrogen or lower alkyl; provided that when $R^7$ is isopropyl, $R^{5A}$ is not hydroxymethyl General formula (9):

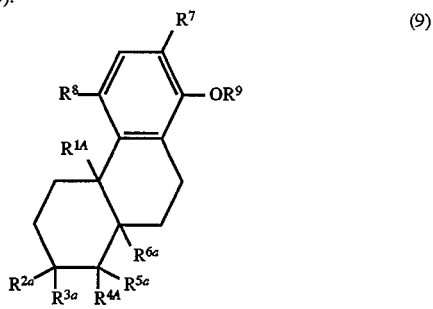

wherein $R^{1A}$, $R^{4A}$ and $R^7$ are as defined above; $R^{2a}$ represents formyl, tri(lower)alkylsilyloxy, trifluoro methylsulfonyloxy or

(wherein $R^{10}$ represents lower alkyl; Ph represents phenyl); $R^{3a}$ represents hydroxy; or $R^{2a}$ and $R^{3a}$, taken together, represent oxo or $R^{10}O$—CH= ($R^{10}$ is as defined above); $R^{3a}$ may form a double bond in combination with $R^{5a}$ which is defined below; $R^{5a}$ represents hydrogen or hydroxy (lower)alkyl or may form a double bond in combination with $R^{3a}$ or $R^{6a}$ which is defined below; $R^{6a}$ represents hydrogen or may form a double bond in combination with $R^{5a}$; $R^8$ represents hydrogen or lower alkoxy; $R^9$ represents lower alkyl; provided that when $R^7$ is isopropyl, $R^{5a}$ is not hydroxymethyl and that when $R^7$ and $R^8$ concurrently represent hydrogen, $R^{5a}$ and $R^{6a}$ are not combined to form a double bond General formula (10):

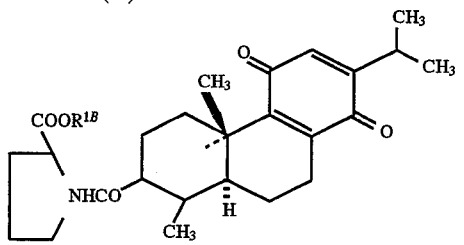

wherein $R^{1B}$ represents lower alkyl

General formula (11):

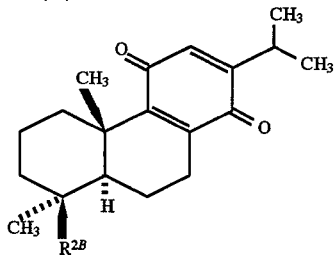

wherein $R^{2B}$ represents hydroxymethyl or carboxyl

General formula (12):

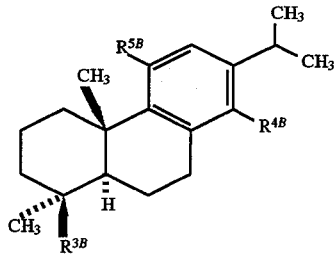

wherein $R^{3B}$ represents lower alkoxycarbonyl or hydroxymethyl; $R^{4B}$ and $R^{5B}$ each represent lower alkoxy.

Each of the groups relevant to the above general formulas (1)–(12) representing the active ingredient compound of this invention includes the following exemplary species.

The lower alkyl includes a straight- or branched-chain alkyl group of 1–6 carbon atoms, such as methyl, ethyl, propyl, isopropyl, butyl, tert-butyl, pentyl and hexyl.

The lower alkanoyl includes a straight- or branched-chain alkanoyl group of 1–6 carbon atoms, such as formyl, acetyl, propionyl, butyryl, isobutyryl, pentanoyl, and hexanoyl.

The lower alkanoyloxy is typically a straight- or branched-chain alkanoyloxy group of 2–6 carbon atoms, such as acetyloxy, propionyloxy, butyryloxy, isobutyryloxy, pentanoyloxy, and hexanoyloxy.

The lower alkoxy includes a straight- or branched-chain alkoxy group of 1–6 carbon atoms, such as methoxy, ethoxy, propoxy, isopropoxy, butoxy, ter-tbutoxy, pentyloxy, and hexyloxy.

The hydroxy(lower)alkyl includes hydroxymethyl, 1-hydroxyethyl, 1-hydroxypropyl, 1-hydroxybutyl, 1-hydroxypentyl, and 1-hydroxyhexyl.

The tri(lower)alkylsilyloxy includes trimethylsilyloxy, triethylsilyloxy, tripropylsilyloxy, tributylsilyloxy, tri-t-butylsilyloxy, tripentylsilyloxy, and trihexylsilyloxy, The lower alkoxycarbonyl includes methoxycarbonyl, ethoxycarbonyl, propoxycarbonyl isopropoxycarbonyl, butoxycarbonyl, tert-butoxycarbonyl, pentyloxycarbonyl, and hexyloxycarbonyl.

All the above phenanthrene derivatives were developed by the inventors of this invention (JP Kokai H4-211035, JP Application H3-224287, JP Application H4-344590, etc.). Some of these derivatives and processes for their production are already known (for example, from JP Kokai H4-211035), whereas the other derivatives can be produced in accordance with the above known processes.

By way of illustration, the above compound (8) can be produced by the processes represented by the following reaction schemes-1 and -2.

[Reaction Scheme-1]

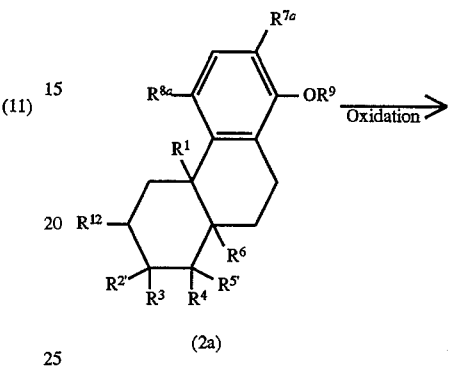

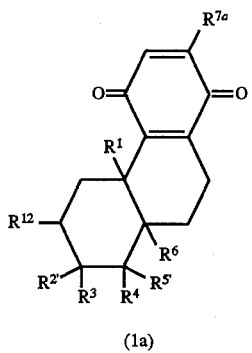

wherein $R^1$, $R^3$, $R^4$ and $R^6$ represent the same as $R^{1A}$, $R^{3A}$, $R^{4A}$ and $R^{6A}$, respectively, of general formula (8); $R^9$ represents lower alkyl; $R^{2'}$ represents either the same as $R^{2A}$ of general formula (8) or any of hydrogen, carboxyl, lower alkoxycarbonyl, hydroxy and lower alkanoyloxy; $R^{5'}$ is either the same as $R^{5A}$ of general formula (8) or represents formyl, carboxyl or lower alkanoyloxymethyl; $R^{7a}$ represents lower alkyl; $R^{8a}$ represents lower alkoxy; and $R^{12}$ represents hydrogen or hydroxy.

The lower alkanoyl of the above lower alkanoyloxy and lower alkanoyloxymethyl include a straight- or branched-chain alkanoyl group of 1–6 carbon atoms, such as formyl, acetyl, propionyl, butyryl, isobutyryl, pentanoyl, and hexanoyl.

The oxidation reaction of compound (2a) in the above reaction scheme-1 can be carried out using an oxidizing agent such as ceric ammonium nitrate [$(NH_4)_2Ce(NO_3)_6$] (hereinafter referred to briefly as CAN), chromic anhydride or the like in an inert solvent such as acetonitrile, dichloromethane, or N,N-dimethylformamide (DMF). The amount of said oxidizing agent can be generally about 1–3 molar equivalents relative to compound (2a) and the reaction is generally conducted at a temperature of about 0°–50° C. and goes to completion in about 10 minutes to about 3 hours to provide the object compound.

[Reaction scheme-2]

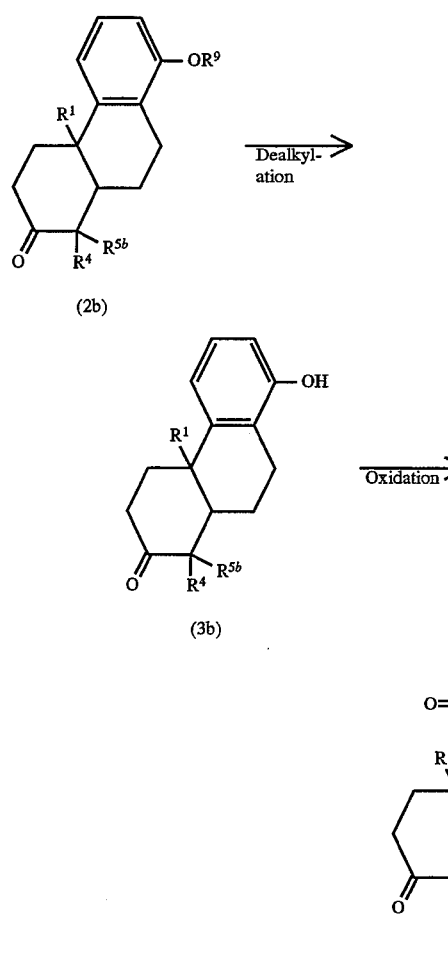

[compound (2c) to compound (2f)] of the above compounds (2a) and (2b) can be produced by the processes represented by the following reaction schemes.

[Reaction scheme-3]

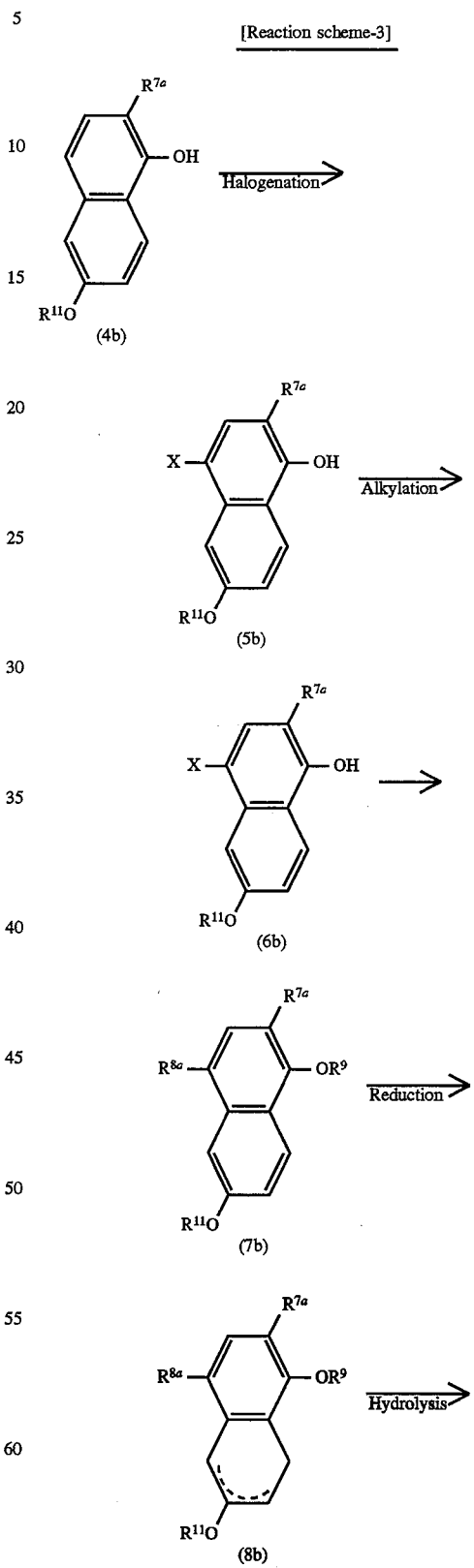

wherein $R^1$, $R^4$ and $R^9$ are as defined above; $R^{5b}$ represents hydroxy(lower)alkyl.

The dealkylation reaction of compound (2b) in the above reaction scheme-2 comprises treating compound (2b) with a dealkylating agent such as boron tribromide, anhydrous ammonium chloride, hydrobromic acid or the like in an inert solvent such as tetrahydrofuran (THF), acetonitrile, dichloromethane, or the like. The amount of said dealkylating agent can be generally about 1–3 molar equivalents relative to compound (2b) and the reaction is generally conducted at a temperature of about –78° C. to 50° C. for about 30 minutes to about 5 hours.

The compound (3b) thus obtained is then oxidized to provide the object compound (1b). This oxidation reaction is carried out in an inert solvent, such as ethanol, dichloromethane, etc., using generally about 1–3 molar equivalents of potassium dinitrosulfonate, potassium nitrosodisulfonate, chromic acid or the like as the oxidizing agent, where necessary in the presence of an additive such as dipotassium hydrogen phosphate, at a temperature of about 0°–50° C. for about 5–20 hours.

The compound (2a) and compound (2b) for use as starting compounds in the above reaction schemes-1 and -2 are invariably novel compounds and some species can be obtained by extractive isolation from the plant *Tripterygium wilfordii Hookfil* var. *regelii Makino* or by extraction and subsequent suitable chemical treatment. The species

-continued
[Reaction scheme-3]

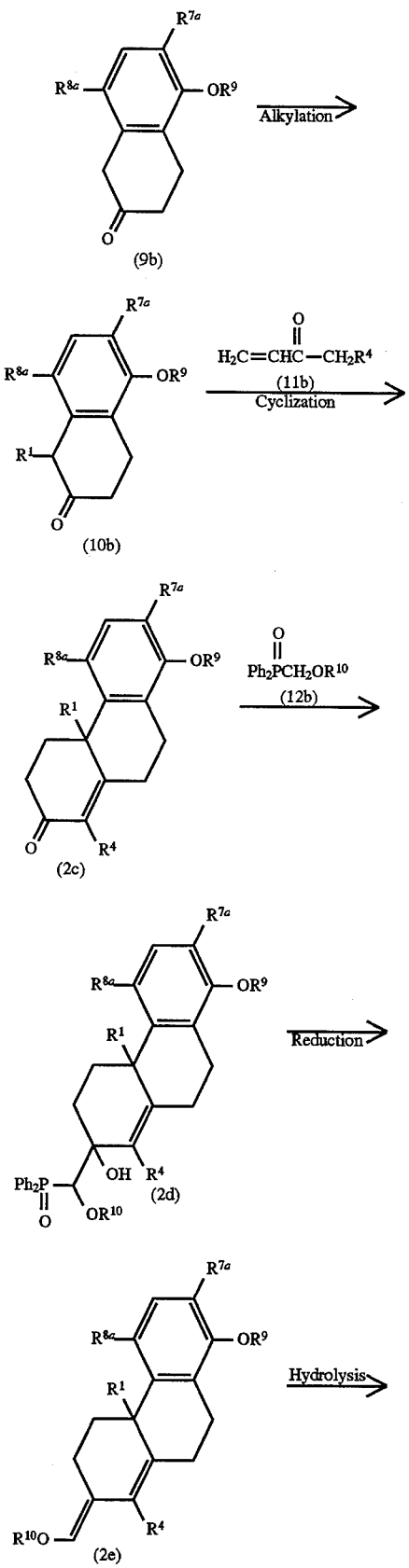

-continued
[Reaction scheme-3]

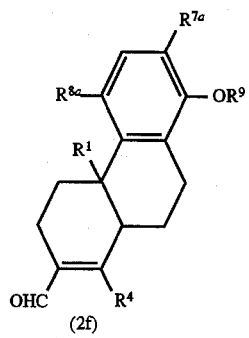

wherein $R^1$, $R^4$, $R^{7a}$, $R^{8a}$, $R^9$ and $R^{10}$ are as defined above; Ph represents phenyl; $R^{11}$ represents lower alkyl; X represents halogen; the broken line indicates the presence of one double bond.

The halogenation reaction of the above compound (4b) is carried out in an inert solvent, such as DMF, chloroform, etc., using about 1–1.5 molar equivalents of a halogenating agent, such as N-bromosuccinimide (NBS), bromine, etc., relative to compound (4b), at a temperature of about 0°–50° C. for about 1–20 hours.

The resulting compound (5b) is alkylated to compound (6b). This alkylation reaction is carried out using an alkylating agent, such as dimethyl sulfate, diazomethane, methyl iodide, etc. in the absence of a solvent or in a suitable inert solvent, such as diethyl ether, acetone, etc., optionally in the presence of an acid acceptor such as aqueous potassium hydroxide solution, potassium carbonate, etc. This reaction is conducted at a temperature of about 0°–30° C. and goes to completion in about 30 minutes to 2 hours.

The subsequent reaction for transformation of compound (6b) to compound (7b) is carried out using a metal (lower) alkoxide, such as sodium methoxide, sodium ethoxide, etc., in the presence of copper(I) iodide in an inert solvent such as DMF, methanol, etc. This reaction is conducted at a temperature of about 50°–100° C. for about 30 minutes to 5 hours.

The reduction reaction of compound (7b) that follows is carried out by treating (7b) with an alkali metal, preferably sodium metal, in a solvent such as methanol, ethanol, liquid ammonia, etc. at a temperature of about 30°–80° C. for 10 minutes to 1 hour.

The resulting compound (8b) is hydrolyzed with an acid, such as oxalic acid, hydrochloric acid, etc., in an inert solvent, such as methanol, ethanol, etc., whereby it is converted to compound (9b). This reaction is conducted at a temperature of about 50°–80° C. and goes to completion in 5–24 hours.

Then, compound (9b) is treated with an alkyl halide, such as methyl iodide, ethyl iodide, etc., in the presence of an amine, such as pyrrolidine, piperidine, etc., in an inert solvent such as benzene, dioxane, toluene, etc., whereby it is alkylated to compound (10b). Preferably, compound (9b) is first reacted with said amine in said inert solvent at a temperature of 20°–50° C. for 3–6 hours and, then, reacted with said alkyl halide at a temperature of about 50°–80° C. for 10–50 hours.

Compound (10b) can be subjected to cyclization reaction with vinyl ketone derivative (11b) to provide the object compound (2c). This cyclization reaction is conducted using 1–1.3 molar equivalents of vinyl ketone derivative (11b) relative to compound (10) in the presence of a base, such as aqueous potassium hydroxide solution, aqueous sodium hydroxide solution, etc., in an inert solvent such as methanol, ethanol, THF and so on. This reaction is conducted at a temperature of about −30° C. to 30° C. for 5–15 hours.

Further, compound (2c) is reacted with compound (12b) to give compound (2d). This reaction is carried out using 1–1.5 molar equivalents of compound (12b) with respect to compound (2c) in the presence of an alkyllithium, e.g. n-butyllithium, and an amine, e.g. diisopropylamine, diethylamine, etc., at a temperature of about −78° C. to −60° C. for 1–3 hours.

The compound (2d) obtained as above is reduced with a hydride compound, such as potassium hydride, sodium hydride, etc., in an inert solvent such as DMF, THF, diethyl ether, etc., whereby it is converted to compound (2e). This reduction reaction is carried out at a temperature of about −30° C. to 10° C. for 30 minutes to 2 hours.

Then, compound (2e) is hydrolyzed to compound (2f). This hydrolysis reaction is carried out with an acid, such as aqueous oxalic acid solution, hydrochloric acid, etc., in an inert solvent such as methanol, ethanol, etc. It is necessary to employ the above-mentioned solvent and acid after thorough deaeration and conduct the reaction in an inert gas atmosphere such as argon, nitrogen; etc. The reaction is conducted at a temperature of 50° C. to the boiling point of the solvent and goes to completion in 1–6 hours.

The resulting compound (2f) can be subjected to the routine oxidation reaction to convert the aldehyde (CHO) group of compound (2f) to a carboxyl (COOH) group, whereby the corresponding compound (2a) in which $R^{2'}$= carboxyl can be obtained.

[Reaction scheme-4]

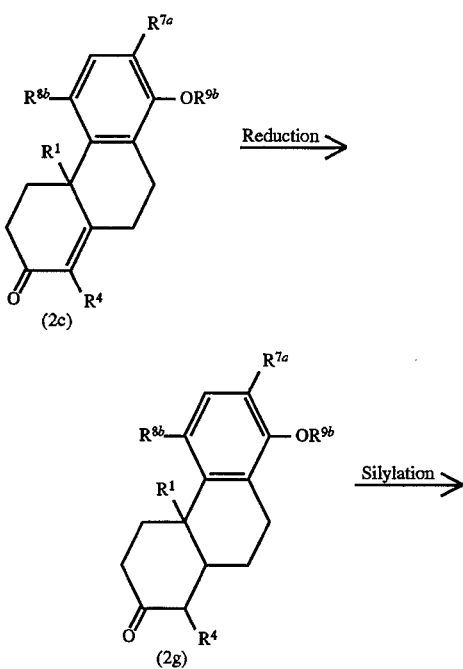

[Reaction scheme-4]
-continued

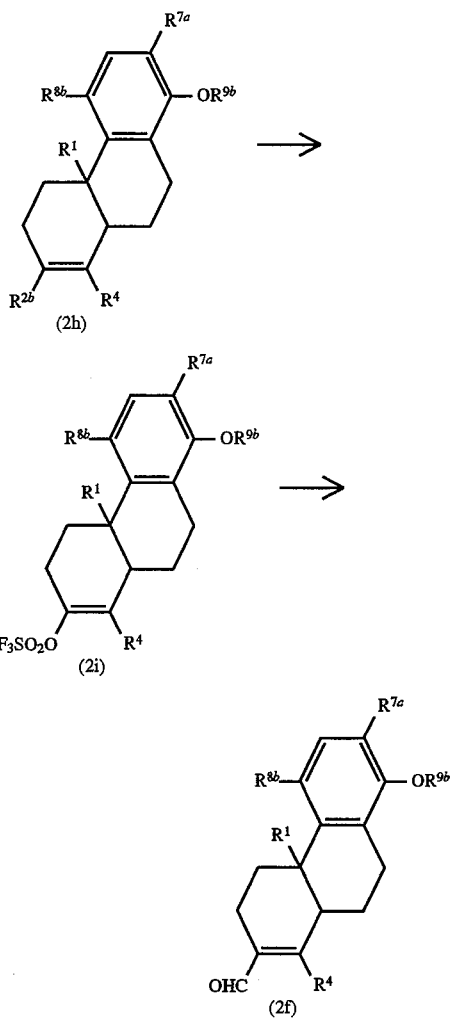

wherein $R^1$, $R^4$ and $R^{7a}$ are as defined above; $R^{8b}$ is the same as $R^{8a}$ or represents lower alkanoyloxy; $R^{9b}$ is the same as $R^9$ or represents hydrogen or lower alkanoyloxy; $R^{2b}$ represents tri(lower)alkylsilyloxy, By the procedures described in the above reaction scheme-4, compound (2f), compound (2g), compound (2h) and compound (2i) can be prepared from compound (2c).

Thus, compound (2c) can be reduced to compound (2g). This reduction reaction is carried out by catalytic reduction in an inert solvent using 1 mol of hydrogen or by using an alkali metal, such as sodium metal, lithium metal, etc., in liquid ammonia (Birch reduction).

Then, the transformation to compound (2h) can be accomplished by subjecting the Birch reaction product of compound (2c) to silylation without isolation and in the state of the metal enolate obtained on removal of ammonia. This silylation reaction is conducted using a silylating agent such as a trialkylsilyl chloride in an inert solvent, such as THF, diethyl ether, etc., in the presence of an acid acceptor such as triethylamine, pyridine or the like. This reaction is conducted at a temperature of about −10° C. to 10° C. for about 10 minutes to 1 hour.

The resulting compound (2h) is treated in the presence of an alkyllithium, e.g. methyllithium, butyllithium, etc., in an inert solvent, such as THF, ether, etc., at a temperature of −10° C. to 30° C. for 30 minutes to 1 hour and, then, treated with N-phenyltrifluoromethanesulfonimide (PhNTf$_2$) at a temperature of about −78° C. to 10° C. for 5–15 hours to give compound (2i).

Then, according to the process of Still et al. [J. Am. Chem. Soc., 108(3), 452 (1986)], this compound (2i) is reacted with carbon monoxide and a tin hydride compound, such as tributyltin hydride, in the presence of lithium chloride and tetrakis(triphenylphosphine)palladium [Pd(Ph$_3$P)$_4$] to give compound (2f). The reaction temperature and time are about 30°–60° C. and about 15–60 hours.

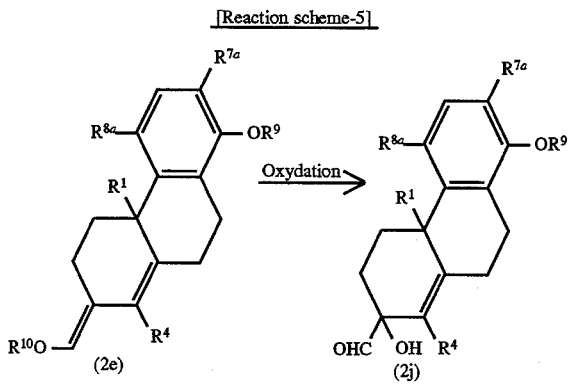

[Reaction scheme-5]

wherein R$^1$, R$^4$, R$^{7a}$, R$^{8a}$, R$^9$ and R$^{10}$ are as defined above.

The oxidation reaction of compound (2e) shown in the above reaction scheme-5 is conducted in accordance with the process of Schumitt et al. [Angev. Chem., 71, 176 (1959)]. Thus, in the presence of oxygen (air) in an aqueous inert solvent such as DMF-H$_2$O, compound (2e) is exposed to palladium(II) chloride-copper(II) chloride complex at a temperature of about 50°–100° C. for about 10–24 hours, whereby compound (2j) can be obtained.

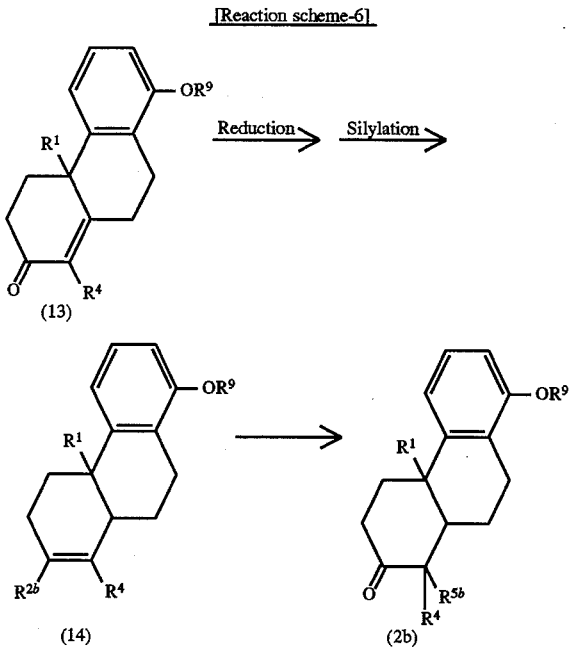

[Reaction scheme-6]

wherein R$^1$, R$^{2b}$, R$^4$, R$^{5b}$ and R$^9$ are as defined above.

Compound (2b) can be obtained from the known compound (13) by the processes indicated in reaction scheme-6.

Thus, compound (13) is first reduced and then silylated to give compound (14). The reduction reaction and silylation reaction can be carried out in the same manner as the reduction reaction and silylation reaction of compound (2c) in reaction scheme-4.

Then, compound (15) is treated with an aldehyde, such as gaseous formaldehyde, in the presence of a desilylating agent, such as tetrabutylammonium fluoride (TBAF), in an inert solvent, such as THF, ether, etc., to give the object compound (2b). This reaction is conducted at a temperature of about −78° C. to 30° C. and goes to completion in about 10 minutes to 1 hour.

The phenanthrene derivatives produced by the respective processes shown in the above reaction schemes can be isolated and purified by the conventional separation procedures. Among such procedures can be mentioned adsorption chromatography, recrystallization, distillative removal of the solvent, precipitation and solvent extraction, to name but a few.

The respective compounds of general formulas (10)–(12) for use as the active ingredient in this invention can be produced by the production technology described in JP Kokai H6-192155 referred to hereinbefore.

The production of said phenanthrene derivatives will be described in detail in the examples (Production Examples) presented hereinafter.

The active ingredient of the nitric oxide synthesis inhibitor composition of this invention includes not only the above-mentioned phenanthrene derivatives but, as far as the derivatives having an acidic function, viz. a phenolic hydroxyl group and/or a carboxyl group, are concerned, the salts formed by the per se conventional salt-forming reaction using a basic compound. The basic compound that can be used for the production of such salts includes the hydroxides, carbonates and hydrides of alkali metals or alkaline earth metals, such as sodium hydroxide, potassium hydroxide, calcium hydroxide, sodium carbonate, potassium carbonate, sodium hydrogen carbonate, sodium hydride, etc. Moreover, organic amines such as methylamine, ethylamine, isopropylamine, morpholine, piperazine, piperidine, 3,4-dimethoxyphenethylamine, etc. can also be used as said salt-forming basic compounds.

The active ingredient compound of this invention can be any of the stereoisomers and optical isomers of said phenanthrene derivatives and salts.

Each of the above phenanthrene derivatives and salts for use as the active ingredient of this invention has activity to inhibit biosynthesis of nitric oxide and, as a consequence, the nitric oxide synthesis inhibitor composition comprising it as the active ingredient according to this invention can be indicated in the therapy or prophylaxis of various nitric oxide-associated diseases, specifically endotoxin shock, hemorrhagic shock, ischemic diseases, and various morbid conditions accompanied by blood pressure depression. The inhibitor composition of this invention inhibits the inducible-type nitric oxide synthase mentioned hereinbefore to specifically inhibit the nitric oxide production by said enzyme and, hence, suppress the abnormal or excess production and release of nitric oxide, thus possessing an additional desirable characteristic.

For use in the inhibitor composition of this invention, the particularly preferred active ingredient compound is selected from among the compounds having a quinone or a hydroquinone structure.

As specific examples, said compounds of general formula (1) can be mentioned. Other preferred examples of the active ingredient are those of general formula (4) wherein R$^3$ represents hydrogen and those of general formula (11).

Particularly preferred, among these active ingredient compounds, are compounds 1–6 as presented hereinafter in Table 10.

The inhibitor composition of this invention can be processed into ordinary pharmaceutical preparations or dosage forms using the conventional pharmaceutically acceptable carriers and administered to man and other animals. The above-mentioned pharmaceutically acceptable carriers and dosage forms (unit dosage forms), methods for their preparation, routes of administration, etc. can be similar to those for the conventional medicinal products. Thus, the unit dosage form includes, among others, tablets, pills, powders, solutions, suspensions, emulsions, granules, capsules, suppositories and injections (solutions, suspensions, etc.) each containing an effective amount of the active ingredient compound of this invention. Any of the above dosage forms can be prepared by the conventional procedures and the carriers for use may also be those conventionally used. Taking tablets as an example, the compound of this invention as the active ingredient is admixed with an excipient such as gelatin, starch, lactose, magnesium stearate, talc, gum arabic, etc. and molded. Capsules are prepared by mixing said active ingredient with an inert pharmaceutically acceptable filler or diluent and filling the resulting mixture in hard gelatin capsule or soft capsule shells. Parenteral dosage forms such as injections are produced by dissolving or suspending the compound of this invention as the active ingredient in a sterilized liquid vehicle. The preferred liquid vehicle to be used is water or physiological saline, and the conventional solubilizer, buffer, local anesthetic or soothing agent, etc. can also be added to the resulting injectable preparations. Moreover, where necessary, a coloring agent, preservative, perfume, flavoring agent, sweetener, etc. as well as other medicinally active substances can be included in said pharmaceutical preparations.

The proportion of the active ingredient phenanthrene derivative or salt thereof in the pharmaceutical composition of this invention is not particularly restricted and can be liberally selected from a broad range but is generally about 1–70 weight % and preferably about 1–30 weight %. The method of administration of the dosage form obtained as above is not particularly restricted. Thus, tablets, pills, powders, granules, capsules, etc. are administered orally, injections (solutions, suspensions, etc.) are administered intravenously either alone or in admixture with the conventional infusion such as glucose infusion or amino acid infusion, or where necessary, administered alone by the intramuscular, intradermal, subcutaneous or intraperitoneal route. While the dosage of the above pharmaceutical composition is suitably selected according to the method of administration, the patient's age, sex and other factors, the severity of disease, etc., the recommended daily dosage in terms of the active ingredient compound of this invention is about 0.1–1000 mg per kg body weight and this dosage can be administered in 1–4 divided doses. It is also recommended that the active ingredient be contained in an amount of about 1–600 mg in each dosage unit.

BEST MODE OF PRACTICING THE INVENTION

For a further explanation of this invention, examples of production of phenanthrene derivatives for use as the active ingredient in this invention are presented below as Examples and some formulation examples and pharmacological test examples using these derivatives are also shown.

Formulation Example 1

| | |
|---|---|
| Compound 1 as listed below in Table 10 | 150 g |
| Avicel (tradename, manufactured by Asahi Kasei Corporation) | 40 g |
| Corn starch | 30 g |
| Magnesium stearate | 2 g |
| Hydroxypropylmethylcellulose | 10 g |
| Polyethylene glycol-6000 | 3 g |
| Castor oil | 40 g |
| Methanol | 40 g |

The above active ingredient compound, Avicel, corn starch and magnesium stearate are milled together and compressed with a dragee R10 mm punch. The resultant tablets are coated with a film coating composition composed of hydroxypropylmethylcellulose, polyethylene glycol-6000, castor oil and methanol to provide film-coated tablets.

Formulation Example 2

| | |
|---|---|
| 3,4,4a,5,8,9,10,10a-Octahydro-1,4a-dimethyl-7-(1-methylethyl)-5,8-dioxo-2-phenanthrenecarboxylic acid | 150.0 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dehydrated sodium lauryl sulfate | 3.0 g |
| Dehydrated magnesium stearate | 3.0 g |
| Ethanol | q.s. |

The above active ingredient, citric acid, lactose, dicalcium phosphate, Pluronic F-68 and sodium lauryl sulfate are mixed and the mixture is sieved through a No. 60 screen. The sieved mixture is wet-granulated using an alcoholic solution containing polyvinyl pyrrolidone, Carbowax 1500 and Carbowax 6000. Where necessary, alcohol is added to the powder to make a paste-like mass, corn starch is then added, and the mixture is continuously blended until homogeneous granules are formed. This mixture, passed through a No. 10 screen, is put in a tray and dried in an oven at 100° C. for 12–14 hours. The dried powder is size-selected using a No. 16 screen and mixed with dehydrated sodium lauryl sulfate and dehydrated magnesium stearate, and using a tablet machine, the resulting composition is compressed to the desired shape to prepare core tablets.

The above core tablets are varnished, dusted over with talc for prevention of moisture absorption, and coated with a primer or base coating dope. The base-coated cores are further serially varnished in a sufficient number of times for the ease of ingestion. The above base coating and varnishing procedures are repeated and a color coating is applied until a desired shade is obtained, followed by drying to provide coated tablets.

EXAMPLE 1

Production of 5,8-dimethoxy-1,4a-dimethyl-7-(1-methylethyl)-4,4a,9,10-tetrahydro-2(3H)-phenanthrenone In 100 ml of DMF was dissolved 5 g of 2-isopropyl-6-methoxy-1-naphthol, and a solution of 4.03 g of N-bromosuccinimide in DMF (50 ml) was added under ice-cooling. The mixture was stirred under ice-cooling for 3 hours. The reaction mixture was then diluted with water and extracted with ethyl acetate and the organic layer was washed with saturated aqueous sodium chloride solution, dried over magnesium sulfate, and concentrated. The resulting crude product was purified by silica gel column chromatography (eluent:diethyl ether:n-hexane:chloroform= 10:50:1) to provide 6.1 g of 4-bromo-2-isopropyl-6-methoxy-1-naphthol. m.p. 81.5°–83.5° C.

$^1$H-NMR (δ:ppm) [CDCl$_3$]: 8.06 (1H, d, J=8.8), 7.58 (1H, s), 7.41 (1H, d, J=2.4), 7.16 (1H, dd, J=8.8, 2.4), 5.18 (1H, brs), 3.96 (3H, s), 3.20 (1H, sept, J=6.8), 1.33 (3H, d, J=6.8)

Then, 1 g of the compound obtained above was added, under ice-cooling, to a solution of 956 mg of potassium hydroxide in 1.7 ml of water, followed by addition of 1.1 ml of dimethyl sulfate, and the mixture was stirred under ice-cooling for 45 minutes. After completion of the reaction, the reaction mixture was diluted with water and extracted with ethyl acetate. The organic layer was washed with saturated aqueous sodium chloride solution, dried over magnesium sulfate, and concentrated. The resulting crude product was purified by silica gel column chromatography (eluent=diethyl ether:n-hexane:chloroform=5:100:2) to provide 1 g of 4-bromo-2-isopropyl-1,6-dimethoxynaphthalene.

m.p. 108°–110° C.

$^1$H-NMR (δ:ppm) [CDCl$_3$]: 7.99 (1H, d, J=9.0), 7.65 (1H, s), 7.43 (1H, d, J=2.3), 7.18 (1H, dd, J=9.0, 2.3), 3.95 (3H, s), 3.89 (3H, s), 3.50 (1H, sept, J=7.3), 1.28 (6H, d, J=7.3)

Then, 3 ml of methanol and 1.7 ml of DMF were added to 631 mg of sodium methoxide, and after addition of 559 mg of copper(I) iodide, the mixture was heated to 90° C. Then, a solution of 901 mg of the above compound in DMF (1.17 ml) was added dropwise and the mixture was refluxed for 2 hours. After cooling, the insoluble solid matter was filtered off and the filtrate was diluted with water and extracted with ethyl acetate. The organic layer was washed with saturated aqueous sodium chloride solution, dried over magnesium sulfate, and concentrated. The resulting crude product was purified by silica gel column chromatography (eluent=diethyl ether:n-hexane:chloroform=5:100:2) to provide 700 mg of 2-isopropyl-1,4,6-trimethoxynaphthalene.

m.p. 80°–81.5° C.

$^1$H-NMR (δ:ppm) [CDCl$_3$]: 7.93 (1H, d, J=9.3), 7.48 (1H, d, J=2.5), 7.16 (1H, dd, J=9.3, 2.5), 6.67 (1H, s), 3.99 (3H, s), 3.92 (3H, s), 3.85 (3H, s), 3.57 (1H, sept, J=7.3), 1.29 (3H, d, J=7.3)

In 100 ml of ethanol was dissolved 16 g of the above compound, and 10.3 g of sodium metal was added at 50°–60° C. over 45 minutes. The mixture was refluxed for 30 minutes, after which 17 ml of ethanol was added and reacted with the excess sodium metal and the mixture was allowed to cool. This reaction mixture was diluted with water and extracted with diethyl ether, and the organic layer was washed with saturated aqueous sodium chloride solution, dried over magnesium sulfate, and concentrated. The resulting crude product was dissolved in 170 ml of methanol and after addition of a solution (30 ml) of 7.3 g of oxalic acid in water, the mixture was refluxed for 21 hours. After cooling, the reaction mixture was diluted with water and extracted with diethyl ether, and the organic layer was washed with saturated sodium chloride solution, dried over magnesium sulfate, and concentrated. The resulting crude product was purified by silica gel column chromatography (eluent=diethyl ether:n-hexane:chloroform=20:140:3) to provide 14.5 g of 5,8-dimethoxy-6-isopropyl-3,4-dihydro-2(1H)-naphthalenone (oil).

$^1$H-NMR (δ:ppm) [CDCl$_3$]: 6.64 (1H, s), 3.81 (3H, s), 3.70 (3H, s), 3.48 (2H, s), 3.36 (1H, sept, J=7.3), 3.11 (2H, dd, J=7.3, 6.8), 2.55 (2H, dd, J=7.3, 6.8), 1.25 (6H, d, J=7.3)

In 91 ml of benzene was dissolved 15.3 g of the above compound and after addition of 12.6 g of molecular sieves 3A and 5.1 g of pyrrolidine, the mixture was stirred at room temperature for 4.5 hours. The mixture was then concentrated under reduced pressure, and after addition of 100 ml of dioxane and 90 g of methyl iodide, the mixture was refluxed for 45 hours. Then, 45 ml of 5% hydrochloric acid was added and the mixture was further refluxed for 3 hours. After cooling, the reaction mixture was diluted with water and extracted with diethyl ether, and the organic layer was washed with saturated sodium chloride solution, dried over magnesium sulfate, and concentrated. The resulting crude product was purified by silica gel column chromatography (eluent=diethyl ether:n-hexane:chloroform=20:140:3) to provide 11.5 g of 5,8-dimethoxy-6-isopropyl-1-methyl-3,4-dihydro-2(1H)-naphthalenone.

$^1$H-NMR (δ:ppm) [CDCl$_3$]: 6.65 (1H, s), 3.81 (3H, s), 3.75 (1H, q, J=7.3), 3.69 (3H, s), 3.36 (1H, sept, J=6.8), 3.28 (1H, ddd, J=16.0, 6.3, 3.7), 2.91 (1H, ddd, J=16.0, 12.3, 4.9), 2.73 (1H, ddd, J=16.4, 4.9, 3.7), 2.40 (1H, ddd, J=16.4, 12.3, 6.3), 1.35 (3H, d, J=7.3), 1.27 (3H, d, J=6.8), 1.23 (3H, d, J=6.8)

An aqueous solution (4 ml) of 1.51 g of potassium hydroxide was cooled to 0° C. and 45 ml of methanol was added. Then, a solution of 6.3 g of the compound obtained above in methanol (9 ml) was added. After the mixture was cooled to –20° C., 2 g of ethyl vinyl ketone was added and the mixture was stirred at –20° C. for 1 hour and, then, at room temperature for 15 hours. After completion of the reaction, diluted hydrochloric acid was added to the reaction mixture to make it acidic and after addition of water, the mixture was extracted with chloroform. The chloroform layer was washed with saturated aqueous sodium chloride solution, dried over magnesium sulfate, and concentrated. The resulting crude product was purified by silica gel column chromatography (eluent=diethyl ether:n-hexane:chloroform=25:125:3) to provide 4.7 g of the object compound.

The structure and physical properties (melting point and $^1$H-NMR) of the compound thus obtained are shown in Table 1.

EXAMPLE 2

Production of 2-hydroxy-5,8-dimethoxy-1,4a-dimethyl-7-(1-methylethyl)-2-(1-methoxy-1-diphenylphosphineoxidomethyl)-2,3,4,4a,9,10-hexahydrophenanthrene A solution of 0.65 ml of diisopropylamine in THF (13.5 ml) was cooled to –78° C. and after addition of 6.1 ml of a THF solution (1.6M) of n-butyllithium, the mixture was stirred for 25 minutes. To this mixture was added a solution of 1.15 g of methoxymethyldiphenylphosphine oxide in 13.5 ml of THF at –78° C. and the mixture was stirred at –78° C. for 25 minutes. To this was added a THF (6 ml) solution of 750 mg of the compound obtained in Example 1 and the mixture was stirred at –78° C. for 2.5 hours. After completion of the reaction, 19 ml of 10% aqueous citric acid was added at –10° C. and the reaction mixture was extracted with ethyl acetate. The organic layer was washed with saturated aqueous sodium chloride solution, dried over magnesium sulfate, and concentrated. The resulting crude product was purified by silica gel column chromatography (eluent=chloroform:ethyl acetate=10:1) to provide 1.3 g of the object compound.

The structure and physical properties of the resulting compound are shown in Table 1.

EXAMPLE 3

Production of 2-(2-methoxyvinylidenyl)-5,8-dimethoxy-1,4a-dimethyl-7-(1-methylethyl)-2,3,4,4a,9,10-hexahydrophenanthrene DMF, 19.6 ml, in which 930 mg of potassium hydride was suspended, was added to a solution of 1.53 g of the compound obtained in Example 2 in DMF (19.6 ml) and the mixture was stirred at 0° C. for 1 hour. To this reaction mixture was added 40 ml of 10% aqueous citric acid solution and the mixture was extracted with ethyl acetate. The organic layer was washed with saturated aqueous sodium chloride solution, dried over magnesium sulfate, and concentrated. The resulting crude product was purified by silica gel column chromatography (eluent=diethyl ether:n-hexane:chloroform=5:50:1) to provide 923 mg of the object compound.

The structure and physical properties of the compound obtained above are shown in Table 1.

EXAMPLES 4 AND 5

Production of 5,8-dimethoxy-1,4a-dimethyl-7-(1-methylethyl)-3,4,4a,9,10,10a-hexahydro-2-phenanthrenaldehyde (trans- and cis-compounds)

In 45 ml of deaerated methanol was dissolved 2.1 g of the compound obtained in Example 3, followed by addition of 690 mg of deaerated oxalic acid-water (7 ml). The mixture was refluxed in an argon atmosphere for 4.5 hours. After cooling, the reaction mixture was diluted with water and extracted with ethyl acetate. The organic layer was washed with saturated sodium chloride solution, dried over magnesium sulfate, and concentrated. The resulting crude product was purified by silica gel column chromatography (eluent= diethyl ether:n-hexane:chloroform= 20:300:3). In this manner, 350 mg of the object compound with the trans-oriented ring junction was obtained from the latter fraction and 1.45 g of the object compound with the cis-oriented ring junction from the former fraction.

The structures and physical properties (m.p. and $^1$H-NMR) of the respective compounds thus obtained are shown in Table 1.

EXAMPLE 6

Production of 5,8-dimethoxy-1,4a-dimethyl-7-(1-methylethyl)-3,4,4a,9,10,10a-hexahydro-2(1H)-phenanthrenone To 15.6 ml of liquid ammonia was added 28.5 mg of lithium metal at −78° C. and the mixture was stirred for 5 minutes. Then, 15.6 ml of a THF solution containing 500 mg of the compound obtained in Example 1 was slowly added dropwise. After the mixture was stirred at −78° C. for 1.5 hours, the ammonia was distilled off and the residue was diluted with water and extracted with diethyl ether. The organic layer was washed with saturated aqueous sodium chloride solution, dried over magnesium sulfate, and concentrated. The resulting crude product was purified by silica gel column chromatography (eluent=diethyl ether:n-hexane:chloroform=5:50:1) to provide 270 mg of the object compound.

The structure and physical properties of the above compound are shown in Table 1.

EXAMPLE 7

Production of 2-hydroxy-5,8-dimethoxy-1,4a-dimethyl-7-(1-methylethyl)-2,3,4,4a,9,10-hexahydro-2-phenanthrenaldehyde To 9.9 ml of DMF-H$_2$O (10:1) were added 211 mg of palladium(II) chloride and 1.3 g of copper(II) chloride and the mixture was stirred at room temperature for 1 hour. To this mixture was added a DMF (13.5 ml) solution of 750 mg of the compound obtained in Example 3 and the mixture was stirred at 70° C. for 21 hours. After completion of the reaction, the solid matter was filtered off and the filtrate was diluted with water and extracted with ethyl acetate.

The organic layer was washed with saturated aqueous sodium chloride solution, dried over magnesium sulfate, and concentrated. The resulting crude product was purified by silica gel column chromatography (eluent=diethyl ether:n-hexane:chloroform=5:50:1) to provide 300 mg of the object compound.

The structure and physical properties of the above compound are shown in Table 1.

In the above chromatography, 150 mg of 5,8-dimethoxy-1,4a-dimethyl-7-(1-methylethyl)-3,4,4a,9-tetrahydro-2-phenanthrenaldehyde was obtained as a byproduct from the former fraction.

m.p.≧107° C. (decomp.)

$^1$H-NMR (δ:ppm) [CDCl$_3$]: 10.31 (1H, s), 6.67 (1H, s), 6.39 (1H, dd, J=5.1, 3.1), 3.84 (3H, s), 3.71 (3H, s), 3.68 (1H, dd, J=14.4, 5.1), 3.50 (1H, dd, J=14.4, 3.1), 3.32 (1H, sept, J=6.8), 3.05–3.11 (1H, m), 2.47–2.55 (1H, m), 2.35 (3H, s), 2.28–2.36 (1H, m), 1.41–1.51 (1H, m), 1.31 (3H, s), 1.26 (3H, d, J=6.8), 1.23 (3H, d, 6.8)

EXAMPLE 8

Production of 1,4a-dimethyl-1-hydroxymethyl-8-methoxy-3,4,4a,9,10,10a-hexahydro-2(1H)-phenanthrenone To 30 ml of liquid ammonia was added 0.82 g of lithium metal at −78° C. and the mixture was stirred for 15 minutes. To this mixture was added a solution prepared by dissolving 5 g of 1,4a-dimethyl-8-methoxy-4,4a,9,10-tetrahydro-2(3H)-phenanthrenone and 3.7 ml of t-butanol in THF (35 ml) and the mixture was stirred at −78° C. for 30 minutes. After completion of the reaction, 9 ml of isoprene was added and reacted with the excess reagent and the ammonia was distilled off under nitrogen gas.

Then, the residue was dissolved in 50 ml of THF and a solution prepared by dissolving 12.8 g of trimethylsilyl chloride and 11.8 g of triethylamine in THF (40 ml) was added. The mixture was stirred under ice-cooling for 30 minutes. The reaction mixture was then diluted with saturated aqueous sodium hydrogen carbonate solution and extracted with diethyl ether. The organic layer was washed with saturated aqueous sodium chloride solution, dried over magnesium sulfate, and concentrated. The resulting crude product was purified by silica gel column chromatography (eluent=ethyl acetate:n-hexane=1:19) to provide 5.95 g of 1,4a-dimethyl-8-methoxy-2-trimethylsilyloxy-3,4,4a,9,10,10a-hexahydrophenanthrene.

m.p. 79° C.

$^1$H-NMR (δ:ppm) [CDCl$_3$]: 6.51–7.10 (3H, m), 3.76 (3H, s), 1.66–2.87 (9H, m), 1.57 (3H, brs), 0.97 (3H, s), 0.10 (9H, s)

To a solution prepared by dissolving 4.9 g of the above compound in THF (80 ml) was added 22.3 ml of a THF solution (1.0M) of tetrabutylammonium fluoride while formaldehyde gas was introduced into the reactor together with nitrogen gas at −78° C. This mixture was stirred at room temperature for 10 minutes, after which it was poured in iced water and extracted with diethyl ether. The organic layer was washed with saturated aqueous sodium chloride solution, dried over magnesium sulfate, and concentrated. The resulting crude product was purified by silica gel column chromatography (eluent= ethyl acetate:n-hexane= 1:4) to provide 3.6 g of the object compound.

The structure and physical properties of the above compound are shown in Table 1.

EXAMPLE 9

Production of 1,4a-dimethyl-5,8-dimethoxy-7-(1-methylethyl)-2-trimethylsilyloxy-3,4,4a,9,10,10a-hexahydrophenanthrene To 30 ml of liquid ammonia was added 127 mg of lithium metal at −78° C. and the mixture was stirred for 15 minutes. To this mixture was added a solution prepared by dissolving 1 g of the compound obtained in Example 1 and 450 mg of t-butanol in THF (7 ml) and the mixture was stirred at −78° C. for 30 minutes. After completion of the reaction, 1.37 ml of isoprene was added and reacted with an excess reagent and the ammonia was distilled off under nitrogen gas.

Then, the residue was dissolved in 8 ml of THF and a solution prepared by dissolving 1.95 g of trimethylsilyl chloride and 2.47 g of triethylamine in THF (7 ml) was added under ice-cooling. The mixture was stirred under ice-cooling for 30 minutes. The reaction mixture was then diluted with saturated aqueous sodium hydrogen carbonate solution and extracted with diethyl ether. The organic layer was washed with saturated aqueous sodium chloride solution, dried over magnesium sulfate, and concentrated. The resulting crude product was purified by silica gel column chromatography (eluent=diethyl ether:n-hexane= 1:20) to provide 930 mg of the object compound.

The structure and physical properties of the above compound are shown in Table 1.

EXAMPLE 10

Production of 1,4a-dimethyl-5,8-dimethoxy-7-(1-methylethyl)-2-trifluoromethylsulfonyloxy-3,4,4a,9,10,10a-hexahydrophenanthrene In 7 ml of THF was dissolved 500 mg of the compound obtained in Example 9, and at 0° C., 1.07 ml of 1.4M methyllithium-diethyl ether was added. The mixture was stirred at 0° C. for 15 minutes and, then, at room temperature for 30 minutes. After the reaction mixture was cooled to −78° C., a solution prepared by dissolving 475 mg of N-phenyltrifluoromethanesulfonimide in THF (7 ml) was added and the mixture was stirred at 0°–5° C. for 9.5 hours. The reaction mixture was diluted with water and extracted with diethyl ether. The organic layer was washed with saturated aqueous sodium chloride solution, dried over magnesium sulfate, and concentrated. The resulting crude product was purified by silica gel column chromatography (eluent=diethyl ether:n-hexane=1:50) to provide 310 mg of the object compound.

The structure and physical properties of the above compound are shown in Table 1.

On the other hand, 402 mg of tetrakis (triphenylphosphine)palladium and 30 mg of lithium chloride were suspended in 8 ml of THF and 160 mg of the compound obtained in Example 10 was added. This mixture was stirred in an argon gas stream at room temperature for 15 minutes. The reaction mixture was then heated to 50° C. and while carbon dioxide gas was bubbled through the mixture, the mixture was stirred for 2 hours. Then, 5 ml of a solution of 118 mg of tributyltin hydride in THF was added dropwise over 3.5 hours at 50° C. The mixture was further stirred at 50° C. for 21 hours. This reaction mixture was diluted with water and extracted with diethyl ether. The organic layer was washed with saturated aqueous sodium chloride solution, dried over magnesium sulfate, and concentrated. The resulting crude product was purified by silica gel column chromatography (eluent=diethyl ether:n-hexane:chloroform=20:300:3) to provide 45 mg of the same compound as the compound obtained in Example 4.

TABLE 1

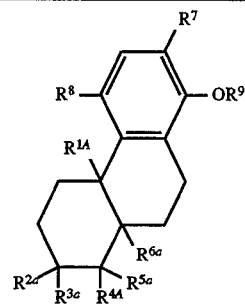

Example 1

$R^{1A}$: —CH$_3$, $R^{2a}$ and $R^{3a}$: =O, $R^{4A}$: —CH$_3$,
$R^{5a}$ and $R^{6a}$: Double bond(carbon-carbon bond),
$R^7$: —CH(CH$_3$)$_2$, $R^8$: —OCH$_3$, $R^9$: —CH$_3$
m.p.: 135–137° C.
$^1$H-NMR(δ: ppm)[CDCl$_3$]:
6.65(1H, s), 3.82(3H, s), 3.65(3H, s),
2.25–3.36(2H, m), 3.03(1H, ddd, J=13.3,
5.1, 2.5), 2.95(1H, ddd, J=12.5, 3.5,
3.5), 2.67(1H, ddd, J=18.1, 14.7, 5.1),
2.41–2.53(2H, m), 2.20–2.29(1H, m),
1.87(3H, s), 1.76–1.88(1H, m), 1.65(3H,
s), 1.24(3H, d, J=7.0), 1.22(3H, d, J= 7.0)

Example 2

$R^{1A}$: —CH$_3$, $R^{2a}$: Ph$_2$P—CH—, $R^{3a}$: —OH,
∥  |
O  OCH$_3$ $R^{4A}$: —CH$_3$, $R^{5a}$ and $R^{6a}$: Double bond(carbon-carbon bond),
$R^7$: —CH(CH$_3$)$_2$, $R^8$: —OCH$_3$, $R^9$: —CH$_3$
m.p.: >95° C.(decomposition)
$^1$H-NMR(δ: ppm) [CDCl$_3$]:
8.10–8.17(2H, m), 7.78–7.85(2H, m),
7.41–7.57(6H, m), 6.60(1H, s), 5.41(1H,
s), 4.16(1H, d, J=9.1), 3.68(3H, s),
3.28(1H, sept, J=6.8), 3.03–3.13(1H,
m), 3.07(3H, s), 2.73–2.80(1H, m), 2.35–
2.45(1H, m), 2.23(1H, ddd, J=13.1, 3.4,
3.4), 1.80–2.13(3H, m), 1.88(3H, s),
1.70–1.80(1H, m), 1.45(3H, s), 1.25(3H,
d, J=6.8), 1.21(3H, d, J=6.8)

Example 3

$R^{1A}$: —CH$_3$, $R^{2a}$ and $R^{3a}$: =CH—OCH$_3$, $R^{4A}$: —CH$_3$,
$R^{5a}$ and $R^{6a}$: Double bond(carbon-carbon bond),
$R^7$: —CH(CH$_3$)$_2$, $R^8$: —OCH$_3$, $R^9$: —CH$_3$
Form: Oil
$^1$H-NMR(δ: ppm) [CDCl$_3$]:
6.61, 6.60(1H, s), 6.10, 5.71(1H, s),

TABLE 1-continued

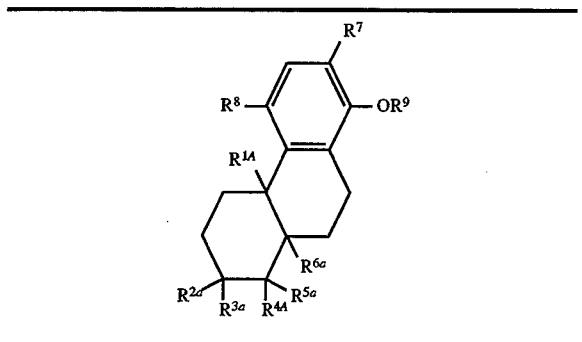

3.80, 3.78(3H, s), 3.68, 3.63(3H, s),
3.63, 3.55(3H, s), 3.25–3.36(1H, m),
3.06–3.17(1H, m), 2.78–2.93(2H, m),
2.61–2.71(1H, m), 2.23–2.48(2H, m),
2.08, 1.80(3H, s), 1.91–2.11(1H, m),
1.51, 1.50(3H, s), 1.18–1.28(3H, d, J=6.8)

Example 4

$R^{1A}$: β-$CH_3$, $R^{2a}$: —CHO,
$R^{3a}$ and $R^{5a}$: Double bond(carbon-carbon bond), $R^{4A}$: —$CH_3$,
$R^{6a}$: α-H, $R^7$: —CH($CH_3$)$_2$, $R^8$: —$OCH_3$,
$R^9$: —$CH_3$
$^1$H-NMR(δ: ppm) [CDCl$_3$]:
10.21(1H, s), 6.61(1H, s), 3.80(3H, s),
3.70(3H, s), 3.31(1H, sept, J=6.8),
3.11(1H, ddd, J=17.5, 5.3, 1.5), 3.03
(1H, ddd, J=13.5, 7.5, 3.3), 2.68(1H,
ddd, J=17.5, 12.7, 6.6), 2.41–2.53(2H,
m), 2.18–2.31(1H, m), 2.23(3H, d, J=
1.5), 1.25–1.68(3H, m), 1.23(3H, d, J=
6.8), 1.22(3H, d, J=6.8), 1.12(3H, s)

Example 5

$R^{1A}$: β-$CH_3$, $R^{2a}$: —CHO,
$R^{3a}$ and $R^{5a}$: Double bond(carbon-carbon bond), $R^{4A}$: —$CH_3$,
$R^{6a}$: β-H, $R^7$: —CH($CH_3$)$_2$, $R^8$: —$OCH_3$,
$R^9$: —$CH_3$
m.p.: 137–139° C.
$^1$H-NMR(δ: ppm) [CDCl$_3$]:
10.18(1H, s), 6.60(1H, s), 3.80(3H, s),
3.66(3H, s), 3.30(1H, sept, J=6.8),
2.95(1H, ddd, J=17.1, 4.4, 4.4), 2.65(1H,
ddd, J=16.8, 11.0, 4.4), 2.26(3H, s),
2.01–2.23(5H, m), 1.75–1.85(1H, m),
1.55–1.65(1H, m), 1.35(3H, s), 1.23(3H,
d, J=6.8), 1.21(3H, d, J=6.8)

Example 6

$R^{1A}$: β-$CH_3$, $R^{2a}$ and $R^{3a}$: =O, $R^{4A}$: α-$CH_3$,
$R^{5a}$: β-H, $R^{6a}$: α-H, $R^7$: —CH($CH_3$)$_2$, $R^8$: —$OCH_3$,
$R^9$: —$CH_3$
$^1$H-NMR(δ: ppm) [CDCl$_3$]:
6.61(1H, s), 3.80(3H, s), 3.67(3H, s),
3.25–3.35(2H, m), 3.01–3.09(1H, m),
2.38–2.65(2H, m), 1.87–1.95(1H, m),
1.55–1.68(2H, m), 1.43–1.55(1H, m),
1.42(3H, s), 1.23(3H, d, J=6.8), 1.22
(3H, d, J=6.8), 1.13(3H, d, J=7.3)

Example 7

$R^{1A}$: —$CH_3$, $R^{2a}$: —CHO, $R^{3a}$: —OH, $R^{4A}$: —$CH_3$,
$R^{5a}$ and $R^{6a}$: Double bond(carbon-carbon bond),
$R^7$: —CH($CH_3$)$_2$, $R^8$: —$OCH_3$, $R^9$: —$CH_3$
m.p.: 177–178° C.
$^1$H-NMR(δ: ppm) [CDCl$_3$]:
9.36(1H, s), 6.62(1H, s), 3.80(3H, s),
3.64(3H, s), 3.53(1H, s), 3.29(1H, sept,
J=6.8), 3.16(1H, ddd, J=16.6, 4.4, 2.5),
2.91(1H, ddd, J=13.2, 3.4, 3.4), 2.79(1H,
ddd, J=12.7, 4.4, 2.5), 2.43–2.53(1H,
m), 2.05–2.17(2H, m), 1.57–1.69(1H, m),
1.61(3H, s), 1.55(3H, s), 1.45(1H, ddd,

TABLE 1-continued

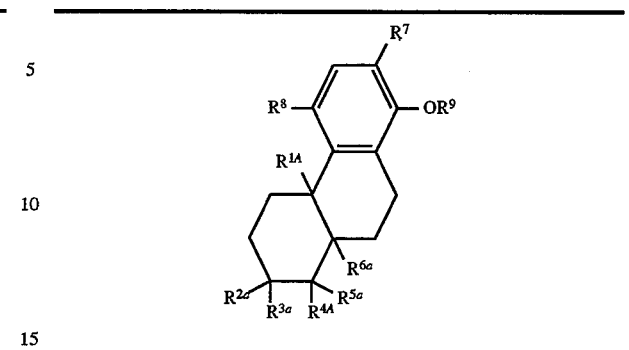

J=14.2, 3.4, 3.4), 1.22(3H, d, J=6.8),
1.21(3H, d, J=6.8)

Example 8

$R^{1A}$: β-$CH_3$, $R^{2a}$ and $R^{3a}$: =O, $R^{4A}$: β-$CH_3$,
$R^{5a}$: α-$CH_2OH$, $R^{6a}$: α-H, $R^7$: H, $R^8$: H,
$R^9$: —$CH_3$
m.p.: 135° C.
$^1$H-NMR(δ: ppm) [CDCl$_3$]:
7.15(1H, dd, J=8.0, 8.0), 6.90(1H, d, J=
8.0), 6.68(1H, d, J=8.0), 3.81(3H, s),
3.70(1H, dd, J=11.2, 6.6), 3.50(1H, dd,
J=11.2, 6.6), 1.60–3.10(10H, m), 1.41
(3H, s), 1.12(3H, s), Example 9

$R^{1A}$: β-$CH_3$, $R^{2a}$: —OSi($CH_3$)$_3$,
$R^{3a}$ and $R^{5a}$: Double bond(carbon-carbon bond), $R^{4A}$: —$CH_3$,
$R^{6a}$: α-H, $R^7$: —CH($CH_3$)$_2$, $R^8$: —$OCH_3$,
$R^9$: —$CH_3$
m.p.: 124–25° C.
$^1$H-NMR(δ: ppm) [CDCl$_3$]:
6.58(1H, s), 3.78(3H, s), 3.68(3H, s),
3.30(1H, sept, J=6.8), 3.10–3.18(1H,
m), 2.97–3.06(1H, m), 2.66(1H, ddd, J=
17.5, 12.2, 6.8), 2.21–2.40(2H, m),
1.98–2.13(2H, m), 1.63(3H, q-like),
1.41–1.53(2H, m), 1.22(6H, d, J=6.8),
1.16(3H, s), 0.19(9H, s)

Example 10

$R^{1A}$: β-$CH_3$, $R^{2a}$: —$OSO_2CF_3$,
$R^{3a}$ and $R^{5a}$: Double bond(carbon-carbon bond), $R^{4A}$: —$CH_3$,
$R^{6a}$: α-H, $R^7$: —CH($CH_3$)$_2$, $R^8$: —$OCH_3$,
$R^9$: —$CH_3$
m.p.: 132.5–133.5° C.
$^1$H-NMR(δ: ppm) [CDCl$_3$]:
6.60(1H, s), 3.79(3H, s), 3.68(3H, s),
3.25–3.37(2H, m), 3.03–3.11(1H, m),
2.68(1H, ddd, J=17.8, 12.2, 6.5),
2.31–2.65(3H, m), 2.03–2.11(1H, m),
1.81(3H, d, J=0.9), 1.48–1.63(2H, m),
1.22(6H, d, J=6.8), 1.21(3H, s)

EXAMPLE 11

Production of 1,4a-dimethyl-7-(1-methylethyl)-5,8-dioxo-3,4,4a,5,8,9,10,10a-octahydro-2-phenanthrenaldehyde (cis-compound)

In 10 ml of acetonitrile was dissolved 310 mg of the compound obtained in Example 5, and after addition of 5 ml of a solution of 1.24 g of CAN in water, the mixture was stirred at room temperature for 30 minutes. This reaction mixture was diluted with water and extracted with chloroform. The organic layer was washed with saturated sodium chloride solution, dried over magnesium sulfate, and concentrated. The resulting crude product was purified by silica gel column chromatography (eluent=diethyl ether:n-hexane:chloroform=10:50:1) to provide 150 mg of the object compound.

The structure and physical properties of the compound obtained above are shown in Table 2.

EXAMPLES 12–14

The compounds of Examples 12–14 were obtained by the same procedure as described in Example 11. The structure and physical properties of these compounds are shown in Table 2.

EXAMPLE 15

Production of 8-hydroxymethyl-4b,8-dimethyl-5,6, 8,8a,9,10-hexahydro-1,4,7(4bH)-phenanthrenetrione In 4 ml of dichloromethane was dissolved 150 mg of the compound obtained in Example 8, and under ice-cooling, 1.2 ml of a solution (1.0M) of boron tribromide in n-hexane was added. The mixture was stirred at 0° C. for 1.5 hours, and then it was diluted with saturated aqueous sodium hydrogen carbonate solution and extracted with ethyl acetate. The organic layer was washed with saturated aqueous sodium chloride solution, dried over magnesium sulfate, and concentrated. In 10 ml of ethanol was dissolved 34 mg of the resulting crude crystals, and after addition of an aqueous solution (6.8 ml) containing 83 mg of potassium dinitrosulfonate and 34 mg of dipotassium hydrogen phosphate, the mixture was stirred at room temperature for 13 hours. The reaction mixture was then diluted with water and extracted with chloroform. The organic layer was washed with saturated sodium chloride solution, dried over magnesium sulfate, and concentrated. The resulting crude product was purified by silica gel column chromatography (eluent=ethyl acetate:n-hexane=1:9) to provide 1 mg of the object compound.

The structure and physical properties of the resulting compound are shown in Table 2.

TABLE 2

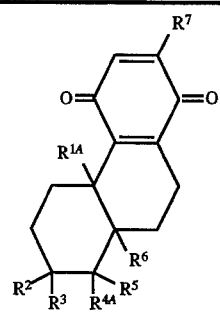

Example 11

$R^{1A}$: β-$CH_3$, $R^2$: —CHO, $R^{4A}$: —$CH_3$,
$R^3$ and $R^5$: Double bond(carbon-carbon bond), $R^6$: β-H,
$R^7$: —CH($CH_3$)$_2$
Form: Oil
$^1$H-NMR(δ: ppm) [$CDCl_3$]:
10.16(1H, s), 6.38(1H, d, J=1.0), 3.00
(1H, septd, J=6.8, 1.0), 2.60(1H, ddd, J=
10.0, 5.0, 5.0), 2.38(1H, ddd, J=19.5,
9.3, 5.7), 2.22(3H, s), 2.01–2.27(2H,
m), 1.93–1.97(1H, m), 1.81–1.89(1H, m),
1.55–1.67(2H, m), 1.31(3H, s), 1.11(6H,
d, J=6.8)

Example 12

$R^{1A}$: —$CH_3$, $R^2$ and $R^3$: =O, $R^{4A}$: —$CH_3$,
$R^5$ and $R^6$: Double bond(carbon-carbon bond),

TABLE 2-continued

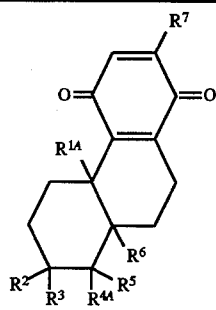

$R^7$: —CH($CH_3$)$_2$
m.p.: 94–95° C.
$^1$H-NMR(δ: ppm) [$CDCl_3$]:
6.41(1H, d, J=1.5), 2.91–3.08(3H, m),
2.80(1H, ddd, J=13.0, 5.2, 2.5), 2.68(1H,
ddd, J=17.3, 14.8, 5.2), 2.47(1H, ddd,
J=17.3, 4.7, 2.5), 2.13–2.31(2H, m),
1.84(3H, d, J=1.0), 1.75–1.87(1H, m),
1.64(3H, s), 1.13(3H, d, J=6.8), 1.12(3H,
d, J=6.8)

EXAMPLE 16

The stem of the plant *Tripterygium wilfordii Hookfil* var. *regelii Makino*, 108 kg, was sliced and extracted with 200 1 of methanol at room temperature for 7 days. The extract thus obtained was concentrated under reduced pressure to provide a crude extract. This crude extract was suspended in 20 l of water and extracted three times with 20 l each of ethyl acetate. The ethyl acetate layers were combined and concentrated under reduced pressure to provide 1300 g of an ethyl acetate extract.

A 1200 g portion of the above ethyl acetate extract was subjected to silica gel column chromatography (Merck silica gel 60, 70–230 mesh, 1500 g, Merck) and serially eluted with 10 l each of 20%, 40%, 60% and 80% ethyl acetate/n-hexane (v/v %) and ethyl acetate and further with 10 l each of 10%, 20% and 30% methanol/ethyl acetate (v/v %) and methanol. The eluates, 500 ml each, were collected to provide fractions (1)–(11).

From fraction (4), among the above fractions, the solvent was distilled off under reduced pressure and of the residue weighing 57 g, 53 g was subjected to silica gel column chromatography (Merck silica gel 60, 70–230 mesh, 1200 g) and fractionally eluted using 10 l of chloroform and 10 l of 5% methanol/chloroform (v/v %) to provide fractions (4-1) to (4-7). Then, the fraction (4-4) (19 g) obtained above was subjected to silica gel column chromatography (Merck silica gel, 70–230 mesh, 500 g) and serially eluted with 2 l each of 75%, 66%, 50% and 33% n-hexane/ethyl acetate (v/v %) and ethyl acetate. Each eluate was collected in a volume of 100 ml to provide fractions (4-4-1) to (4-4-11).

The fraction (4-4-6) thus obtained, 3.5 g, was further subjected to silica gel column chromatography (Merck silica gel, 70–230 mesh, 200 g) and eluted with 2 l of 95% chloroform/methanol (v/v %) and the eluate was subjected to Sephadex LH-20 (500 ml, Pharmacia) column chromatography twice using 90% methanol/chloroform as the eluent. The eluate thus obtained was further subjected to silica gel column chromatography (Merch silica gel, 70–230 mesh, 100 g) and fractionally eluted with 1 l of 99% chloroform/methanol (v/v %) for purification. The product thus obtained was recrystallized from methanol to provide 0.057 g of 1,2,3,4,4a,5,8,9,10,10a-decahydro-1,4a-dimethyl-7-(1-methylethyl)-5,8-dioxo-1-phenanthrenecarboxylic acid as yellow needles.

m.p. 207°–209° C.

$[\alpha]_D$=+80.5 (CHCl$_3$;c 1.0)

IRv$^{KBr}_{max}$cm$^{-1}$: 3400, 1730, 1696, 1650, 1470, 1270, 1240, 913, 800

UVλ$^{MeOH}_{max}$nm (ε): 260 (15300)

$^1$H-NMR (CDCl$_3$) δppm: 1.01 (3H×2, d, J=6.8 Hz, H-16, 17), 1.22 (3H, s, H-20), 1.31 (3H, s, H-18), 1.0–1.2 (2H, m, H-1, H-3), 1.30 (1H, m, H-5), 1.55 (1H, brd, J=14.2 Hz, H-2), 1.79 (1H, m, H-6), 1.96 (1H, m, H-2), 2.15–2.29 (3H, m, H-3, H-6, H-7), 2.70 (1H, brd, J=16.1 Hz, H-1), 2.75 (1H, dd, J=19.5, 5.9 Hz, H-7), 2.99 (1H, sept, J=6.8 Hz, H-15), 6.33 (1H, s, H-15)

EI-MS m/z (rel. int.): 330 [M]$^+$ (35), 315 [M—CH$_3$]$^+$ (15), 284 (55), 269 (100), 227 (44), 204 (39)

HR-MS m/z: 330.1864 [M]$^+$ (C$_{20}$H$_{26}$O$_4$=330.1831)

EXAMPLE 17

The unbarked stem of the plant *Tripterygium wilfordii Hookfil* var. *regelii Makino*, 18.4 kg, was sliced and extracted with 20 l of methanol at 60° C. for 6 hours. This procedure was repeated 3 times. The extract thus obtained was concentrated under reduced pressure to provide a crude extract (680 g). This crude extract was suspended in 2 l of water and extracted thrice with 2 l each of ethyl acetate. The ethyl acetate layers were combined and concentrated under reduced pressure to provide 140 g of an ethyl acetate extract.

This ethyl acetate extract, 140 g, was subjected to silica gel column chromatography (Merck silica gel 70–230 mesh, 1 kg) and serially eluted with 3 l each of 75%, 66% 20% and 33% n-hexane/ethyl acetate (v/v %) and ethyl acetate and further with 2 l each of 95%, 90% and 80% ethyl acetate/ methanol and methanol. The eluates, 300 ml each, were collected to provide fractions (1)–(20).

From fraction (10), among the above fractions, the solvent was distilled off, and of the residue weighing 6.5 g, 6.37 g was subjected to Sephadex LH-20 (500 ml, Pharmacia) column chromatography once. Fractional elution was carried out with 2 l of methanol to provide fractions (10-1) to (10-7).

Then, 1.24 g of fraction (10-3) obtained was subjected to silica gel column chromatography (Merck silica gel, 70–230 mesh, 200 g) and eluted with 1 l each of 98% and 95% chloroform/methanol (v/v %) and then with 1 l of 98% chloroform/methanol (v/v %). The eluate was further subjected to high performance liquid chromatography (ODS) using 500 ml of 90% methanol/water (v/v %) as the eluent. The eluate was further purified by silica gel column chromatography (Merck silica gel, 70–230 mesh, 100 g) using 500 ml of 66% n-hexane/ethyl acetate as the eluent to provide 24 mg of 1,2,3,4,4a,5,8,9,10,10a-decahydro-1-(hydroxymethyl)-1,4a-dimethyl-7-(1-methylethyl)-5,8-dioxo-phenanthrene as amorphous powdery crystals.

IRv$^{KBr}_{max}$cm$^{-1}$: 3370, 1710, 1650, 1600, 1290, 1265, 1080, 906, 755

UVλ$^{MeOH}_{max}$nm (ε): 260 (11800)

$^1$H-NMR (CDCl$_3$) δppm: 1.04 (3H, s, H-18), 1.09, 2.00 (each 3H, d, J=6.8 Hz, H-16, 17), 1.24 (1H, brd, J=11.2 Hz, H-5), 1.28 (3H, s, H-20), 2.44 (1H, m, H-6), 1.53 (1H, m, H-2), 1.68 (1H, m, H-2), 1.80 (1H, brd, J=13.6 Hz, Heq-3), 1.99 (1H, dd, J=13.6, 6.8 Hz, Heq-6), 2.28 (1H, ddd, J=20.4, 11.6, 7.2 Hz, Hax-7), 2.69 (1H, dd, J=20.4, 5.2 Hz, Heq-7), 2.75 (1H, brd, J=13.2 Hz, Heq-1), 2.98 (1H, septd, J=7.2, 1.0 Hz, H-15), 3.56, 3.78 (each 1H, ABq, J=11.2 Hz, H-19), 6.32 (1H, d, J=1.0 Hz, H-12)

EI-MS m/z (rel. int.): 316 [M]$^+$ (85), 301 [M—CH$_3$]$^+$ (12), 298 [M—H$_2$O]$^+$ (22), 285 (42), 283 [M—CH$_3$—H$_2$O]$^+$ (100), 241 (46), 203 (58), 91 (42), 43 (52)

HR-MS m/z: 316.2073 [M]$^+$ (C$_{20}$H$_{28}$O$_3$=316.2038)

EXAMPLE 18

To 1.5 ml of a DMF solution containing 100 mg of 3,4,4a,5,8,9,10,10a-octahydro-1,4a-dimethyl-7-(1-methylethyl)-5,8-dioxo-2-phenanthrenecarboxylic acid as obtained by the same extraction procedure as described in Example 16 and 55 mg of proline methyl ester hydrochloride was added 30.8 mg of triethylamine under ice-cooling and the mixture was stirred for 5 minutes. To this mixture was added 0.5 ml of a DMF solution containing 54.7 mg of DEPC under ice-cooling followed by addition of 0.5 ml of a DMF solution containing 92.4 mg of triethylamine, and the mixture was stirred at room temperature for 30 minutes. The reaction mixture was then diluted with water and extracted with ethyl acetate. The organic layer was washed with saturated aqueous sodium chloride solution, dried over anhydrous magnesium sulfate, and concentrated. The resulting crude product was purified by silica gel column chromatography (eluent=chromatography:ethyl acetate=10:1) to provide 100 mg (74.7%) of 3,4,4a,5,8,9,10,10a-octahydro-1,4a-dimethyl-7-(1-methylethyl)-5,8-dioxo-2-phenanthrenecarboxamideproline methyl ester.

EXAMPLE 19

A 50 ml quantity of the compound obtained in Example 16 was dissolved in 2 ml of THF at room temperature and this solution was added to a solution prepared by dissolving 800 mg of Na$_2$S$_2$O$_4$ in 3 ml of water, followed by stirring. After 3 hours of stirring, the reaction mixture was diluted with water and extracted with diethyl ether. The extract was washed with saturated aqueous sodium chloride solution and dried over anhydrous MgSO$_4$, and the solvent was distilled off to give a residue. This residue was dissolved in 2 ml of acetone and after addition of 190 ml of K$_2$CO$_3$ and 177 mg of methyl sulfate to the solution, the mixture was refluxed for 2 hours. The reaction mixture was cooled to 0° C. and the whole solution was neutralized with 10% hydrochloric acid and extracted with diethyl ether. The extract was washed with saturated aqueous sodium chloride solution and dried over anhydrous MgSO$_4$ and the solvent was distilled off to provide a residue.

This residue was subjected to silica gel column chromatography and eluted with 95% n-hexane/ethyl acetate (v/v %) to provide 49 mg of methyl 1,2,3,4,4a,9,10,10a-octahydro-5,8-dimethoxy-1,4a-dimethyl-7-(1-methylethyl)-1-phenanthrenecarboxylate.

mp 133°–135° C.

$[\alpha]_D$=+163.6 (MeOH; c 0.26)

IRv$^{KBr}_{max}$cm$^{-1}$: 1719

$^1$H-NMR (200Mhz) (CDCl$_3$) δppm: 1.12 (3H, s), 1.21 (3H×2, d, J=7.1 Hz), 1.27 (3H, s), 1.40–2.66 (9H, m), 2.97–3.40 (3H, m), 3.65 (3H, s), 3.68 (3H, s), 3.76 (3H, s), 6.57 (1H, s)

HR-MS m/z: 374.2437 [M]$^+$ (C$_{23}$H$_{34}$O$_4$=374.2456)

EXAMPLE 20

In 0.5 ml of dried THF was dissolved 38 mg of the compound obtained in Example 19, and at 0° C., this solution was added dropwise to a suspension prepared by adding 30 mg of LiAlH₄ to 0.5 ml of dried THF. The mixture was stirred at room temperature for 30 minutes, after which aqueous diethyl ether was added cautiously at 0° C. This reaction mixture was filtered through Celite. The filtrate was dried over MgSO₄ and the solvent was distilled off to give an oily residue. This residue was purified by silica gel column chromatography (n-hexane:ethyl acetate=9:1 (v/v %) to provide 31 mg of 1,2,3,4,4a,9,10,10a-octahydro-(hydroxymethyl)-5,8-dimethoxy-1,4a-dimethyl-7-(1-methylethyl)phenanthrene as colorless oil.

$[\alpha]_D$=+99.3 (MeOH; c 0.61)

$IRv^{KBr}_{max}cm^{-1}$: 3631

¹H-NMR (200 Mhz) (CDCl₃) δppm: 1.07 (3H, s), 1.21 (3H×2, d, J=6.8 Hz), 1.28 (3H, s), 1.34–2.11 (8H, m), 2.49–3.40 (3H, m), 3.58 (2H, d, J=10.7 Hz), 3.66 (3H, s), 3.77 (3H, s), 3.84 (2H, d, J=10.7 Hz), 6.57 (1H, s)

HR-MS m/z: 346.2505 [M]⁺ (C₂₂H₃₄O₃=346.2507)

EXAMPLE 21

In 10 ml of THF was dissolved 300 mg of 3,4,4a,5,8,9,10,10a-octahydro-1,4a-dimethyl-7-(1-methylethyl)-5,8-dioxo-2-phenanthrenecarboxylic acid obtained by the same extraction procedure as in Example 16, followed by addition of 16 ml of an aqueous solution containing 1.6 g of sodium dithionite, and the mixture was stirred at room temperature for 30 minutes. The reaction mixture was diluted with water and extracted with diethyl ether. The organic layer was washed with saturated aqueous sodium chloride solution, dried over anhydrous magnesium sulfate, and concentrated. The resulting crude product was purified by silica gel column chromatography (eluent=chloroform:methanol= 100:1) to provide 290 mg of 3,4,4a,9,10,10a-hexahydro-5,8-dihydroxy-1,4a-dimethyl-7-(1-methylethyl)-2-phenanthrenecarboxylic acid.

m.p.≥127° C. (decomp.)

¹H-NMR (DMSO-d₆) δppm: 1.06 (3H, s), 1.07 (3H, d, J=6.7 Hz), 1.10 (3H, d, J=6.7 Hz), 1.21–1.50 (2H, m), 1.97 (3H, s), 2.05–2.55 (5H, m), 2.81 (1H, dd, J=17.5, 4.4 Hz), 3.10–3.33 (2H, m), 6.42 (1H, s), 7.18 (1H, s), 8.47 (1H, s), 12.15 (1H, brs)

Pharmacological Test Example 1

Determination of the relaxation response of the isolated blood vessel (1) Preparation of an aortic ring segment specimen with the endothelium removed The thoracic aorta was excised from male Wistar rats (8–10 weeks old) and immediately stripped off the residual blood. The surrounding adipose and connective tissues were thoroughly removed under the stereoscopic microscope and a ring segment of about 3 mm width was prepared. A cotton thread of suitable size was passed through the vascular lumen and the endothelium was abraded off by reciprocating the thread several times.

A couple of stainless steel wires were inserted into the lumen of the ring segment taking care not to injure the vessel and the segment was suspended in a 10 ml organ bath (maintained at a constant temperature of 34° C.) filled by a nutrient fluid.

One stainless wire was anchored to a holder means and the other was connected to an isometric transducer (Nihon Kohden, TB-651T). A static tension of 1.0 g was applied to the specimen beforehand and maintained through the experiment.

Disappearance of the relaxation response to 1 µM acetylcholine, an endothelium-dependent vascular relaxant, was checked 1 to 2 hours after setting the specimen on a measuring device, and the disappearance meant that the endothelial cells had been functionally impaired. The same procedure was repeated after completion of the experiment to confirm that the function of endothelial cells had hot been restored with time.

Krebs solution was used as the nutrient fluid which was aerated with a mixture gas of 95% O₂-5% CO₂. The Ph of the Krebs solution under the above mixture gas aerating was about 7.4, and the composition of the solution was as follows. NaCl 115.3 mM, KCl 4.7 mM, CaCl₂ 2.5 mM, MgSO₄ 1.2 mM, KH₂PO₄ 1.2 mM, NaHCO₃ 25.0 mM and glucose 11.1 mM.

Moreover, in order to accelerate the induction of nitric oxide synthase in the vascular smooth muscle, either 100 ng/ml of lipopolysaccharide (LPS) or 0.3 ng/ml of recombinant interleukin-1β (rIL-1β) was added to the nutrient fluid.

(2) Assay of vascular relaxation response

To determine the relaxation response, the specimen was contracted with phenylephrine (1 µM) beforehand and when the tonus had become steady, the test compound was cumulatively applied.

To assay the response to the test compound, the change in tension of the specimen was isometrically recorded on a recorder.

The vascular relaxation rate (%) was determined as % of the contraction induced by 1 µM of phenylephrine.

(3) Results

The results obtained by applying (added to the nutrient fluid) the active ingredient compounds 1–6 of the present invention, shown below in Table 10, immediately after the excision of the blood vessel and observing the vessel 8–10 hours after its excision (relaxation rate (%), relative % with the contraction due to 1 µM of phenylephrine being taken as 100%) are shown, test compound by test compound, in Tables 11–16 (LPS was used as NO synthase induction promotor). The corresponding results (for the active ingredient compound 1 of the present invention) obtained using rIL-1β as an NO synthase induction promotor are shown in Table 17.

TABLE 10

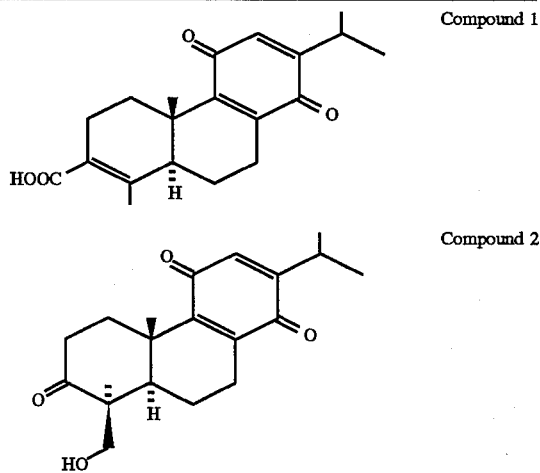

TABLE 10-continued

Compound 3

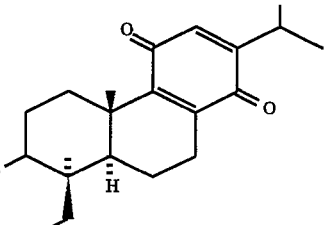

Compound 4

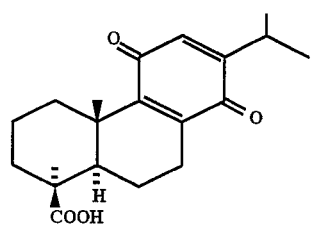

Compound 5

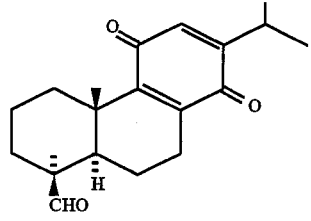

Compound 6

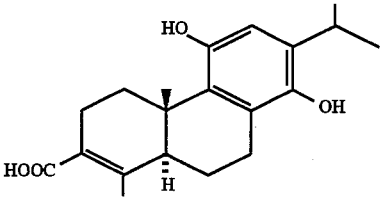

TABLE 11

| Arginine (M) | Relaxation rate (% ± S.E.) Active ingredient compound 1 (μM) | | |
|---|---|---|---|
| | 0 (n = 8) | 10 (n = 8) | 30 (n = 8) |
| $3 \times 10^{-7}$ | 2.0 ± 1.0 | NT | NT |
| $1 \times 10^{-6}$ | 9.4 ± 2.8 | 0.5 ± 0.5 | 0.0 ± 0.0 |
| $3 \times 10^{-6}$ | 46.7 ± 4.3 | 2.7 ± 1.6 | 0.0 ± 0.0 |
| $1 \times 10^{-5}$ | 75.6 ± 4.3 | 12.4 ± 4.4 | 0.0 ± 0.0 |
| $3 \times 10^{-5}$ | 86.3 ± 3.0 | 24.0 ± 5.8 | 0.0 ± 0.0 |
| $1 \times 10^{-4}$ | 92.5 ± 2.0 | 31.4 ± 6.2 | 0.0 ± 0.0 |
| $3 \times 10^{-4}$ | NT | 33.9 ± 6.2 | 0.0 ± 0.0 |

NT: Not tested

TABLE 12

| Arginine (M) | Relaxation rate (% ± S.E.) Active ingredient compound 2 (μM) | |
|---|---|---|
| | 0 (n = 5) | 30 (n = 5) |
| $3 \times 10^{-7}$ | NT | NT |
| $1 \times 10^{-6}$ | 12.9 ± 5.5 | 0.0 ± 0.0 |
| $3 \times 10^{-6}$ | 43.3 ± 8.9 | 0.0 ± 0.0 |
| $1 \times 10^{-5}$ | 81.2 ± 4.2 | 0.0 ± 0.0 |

TABLE 12-continued

| Arginine (M) | Relaxation rate (% ± S.E.) Active ingredient compound 2 (μM) | |
|---|---|---|
| | 0 (n = 5) | 30 (n = 5) |
| $3 \times 10^{-5}$ | 92.7 ± 3.6 | 0.0 ± 0.0 |
| $1 \times 10^{-4}$ | 96.7 ± 1.3 | 0.8 ± 0.8 |
| $3 \times 10^{-4}$ | 99.2 ± 0.8 | 1.3 ± 1.3 |

NT: Not tested

TABLE 13

| Arginine (M) | Relaxation rate (% ± S.E.) Active ingredient compound 3 (μM) | |
|---|---|---|
| | 0 (n = 4) | 30 (n = 4) |
| $3 \times 10^{-7}$ | NT | NT |
| $1 \times 10^{-6}$ | 7.6 ± 6.7 | 0.0 ± 0.0 |
| $3 \times 10^{-6}$ | 20.4 ± 13.6 | 0.0 ± 0.0 |
| $1 \times 10^{-5}$ | 58.2 ± 12.8 | 0.0 ± 0.0 |
| $3 \times 10^{-5}$ | 81.3 ± 10.9 | 0.0 ± 0.0 |
| $1 \times 10^{-4}$ | 88.3 ± 8.1 | 0.0 ± 0.0 |
| $3 \times 10^{-4}$ | NT | NT |

NT: Not tested

TABLE 14

| Arginine (M) | Relaxation rate (% ± S.E.) Active ingredient compound 4 (μM) | |
|---|---|---|
| | 0 (n = 3) | 30 (n = 3) |
| $3 \times 10^{-7}$ | NT | NT |
| $1 \times 10^{-6}$ | 0.0 ± 0.0 | 0.0 ± 0.0 |
| $3 \times 10^{-6}$ | 14.2 ± 10.4 | 0.0 ± 0.0 |
| $1 \times 10^{-5}$ | 57.8 ± 12.0 | 0.0 ± 0.0 |
| $3 \times 10^{-5}$ | 89.1 ± 4.6 | 0.0 ± 0.0 |
| $1 \times 10^{-4}$ | 98.0 ± 1.3 | 0.0 ± 0.0 |
| $3 \times 10^{-4}$ | 99.5 ± 0.5 | 0.0 ± 0.0 |

NT: Not tested

TABLE 15

| Arginine (M) | Relaxation rate (% ± S.E.) Active ingredient compound 5 (μM) | |
|---|---|---|
| | 0 (n = 4) | 30 (n = 5) |
| $3 \times 10^{-7}$ | NT | NT |
| $1 \times 10^{-6}$ | 3.2 ± 2.2 | 0.0 ± 0.0 |
| $3 \times 10^{-6}$ | 22.2 ± 9.6 | 0.0 ± 0.0 |
| $1 \times 10^{-5}$ | 68.6 ± 9.1 | 0.0 ± 0.0 |
| $3 \times 10^{-5}$ | 90.2 ± 0.5 | 0.4 ± 0.4 |
| $1 \times 10^{-4}$ | 96.9 ± 1.3 | 1.4 ± 1.4 |
| $3 \times 10^{-4}$ | NT | 2.0 ± 2.0 |

NT: Not tested

TABLE 16

| | Relaxation rate (% ± S.E.) Active ingredient compound 6 (μM) | |
|---|---|---|
| Arginine (M) | 0 (n = 5) | 30 (n = 5) |
| $3 \times 10^{-7}$ | NT | NT |
| $1 \times 10^{-6}$ | 2.7 ± 1.2 | 0.0 ± 0.0 |
| $3 \times 10^{-6}$ | 33.3 ± 10.6 | 1.5 ± 1.5 |
| $1 \times 10^{-5}$ | 72.1 ± 8.5 | 4.5 ± 4.5 |
| $3 \times 10^{-5}$ | 89.9 ± 5.8 | 11.5 ± 9.2 |
| $1 \times 10^{-4}$ | 96.4 ± 2.3 | 13.2 ± 10.4 |
| $3 \times 10^{-4}$ | 98.4 ± 1.3 | 13.7 ± 10.3 |

NT: Not tested

TABLE 17

| | Relaxation rate (% ± S.E.) Active ingredient compound 1 (μM) | | |
|---|---|---|---|
| Arginine (M) | 0 (n = 3) | 30 (n = 3) | 100 (n = 3) |
| $3 \times 10^{-7}$ | NT | NT | NT |
| $1 \times 10^{-6}$ | 23.1 ± 5.1 | NT | NT |
| $3 \times 10^{-6}$ | 53.0 ± 8.3 | 0.0 ± 0.0 | NT |
| $1 \times 10^{-5}$ | 79.0 ± 8.5 | 7.2 ± 4.4 | 0.0 ± 0.0 |
| $3 \times 10^{-5}$ | 93.0 ± 5.6 | 23.0 ± 12.0 | 0.0 ± 0.0 |
| $1 \times 10^{-4}$ | 98.0 ± 2.1 | 36.0 ± 12.0 | 0.0 ± 0.0 |
| $3 \times 10^{-4}$ | NT | 45.0 ± 8.6 | 0.0 ± 0.0 |
| $1 \times 10^{-3}$ | NT | 48.0 ± 6.8 | 0.0 ± 0.0 |

NT: Not tested

From the above tables, it is apparent that when the active ingredient compound of the present invention (30 μM concentration in the nutrient fluid) is used, no arginine-induced relaxation develops in the blood vessel even 8–10 hours after the excision.

In addition, Table 18 shows the effect of the active ingredient compound of the present invention on the relaxation response to nitroprusside as assayed in the same manner as in the above experiment.

TABLE 18

| | Relaxation rate (% ± S.E.) Active ingredient compound 1 (μM) | |
|---|---|---|
| Nitroprusside (M) | 0 (n = 8) | 30 (n = 8) |
| $1 \times 10^{-10}$ | 0.0 ± 0.0 | 1.9 ± 1.9 |
| $3 \times 10^{-10}$ | 8.5 ± 2.9 | 8.4 ± 4.3 |
| $1 \times 10^{-9}$ | 55.6 ± 7.2 | 42.9 ± 6.9 |
| $3 \times 10^{-9}$ | 87.0 ± 2.8 | 84.9 ± 3.0 |
| $1 \times 10^{-8}$ | 97.4 ± 1.8 | 97.1 ± 1.2 |
| $3 \times 10^{-8}$ | 98.4 ± 1.4 | 99.2 ± 0.8 |

From the above table, it is apparent that the active ingredient compound of the present invention never affects on the relaxation effect of nitroprusside which acts directly on smooth muscle to relax the blood vessel.

INDUSTRIAL APPLICABILITY

The nitric oxide synthesis inhibitor of the resent invention is useful for the prophylaxis and therapy of various diseases associated with nitric oxide, such as endotoxin shock.

We claim:

1. A method of treating a nitric oxide-associated disease comprising, administering to a subject in need thereof a pharmacologically effective amount of at least one phenanthrene derivative selected from the group consisting of the compounds of the following formulas (1) through (12), or a salt thereof, as an active ingredient:

Formula (1)

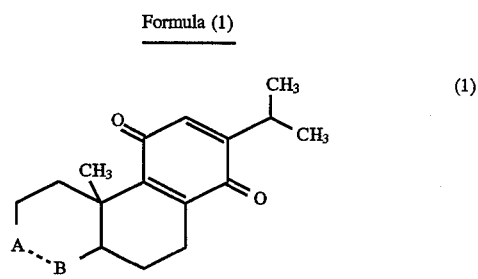
(1)

wherein the —A . . . B— group is represented by

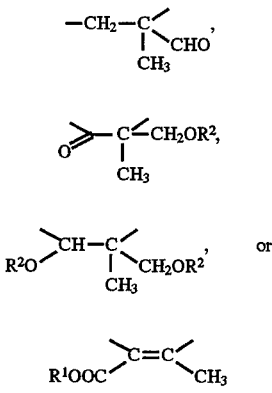

wherein $R^1$ represents a hydrogen atom or a lower alkyl group; and $R^2$ represents a hydrogen atom or a lower alkanoyl group;

Formula (2)

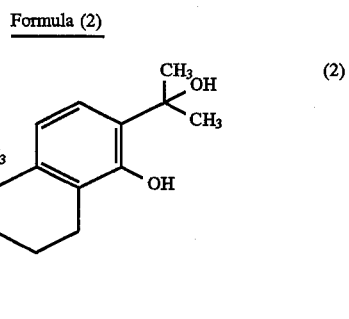
(2)

Formula (3)

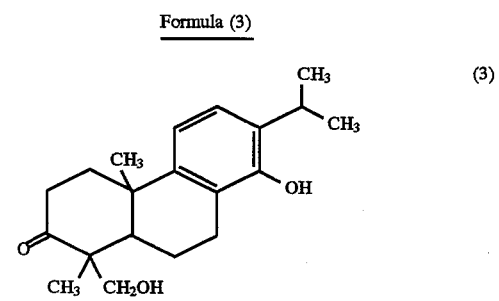
(3)

Formula (4)

(4)

wherein R³ represents a hydrogen atom or a methyl group;

Formula (5)

(5)

Formula (6)

(6)

wherein R⁴ represents a lower alkanoyloxy group; and R² represents a hydrogen atom or a lower alkanoyl group;

Formula (7)

(7)

wherein R⁵ and R⁶ each represents a lower alkoxy group;

Formula (8)

(8)

wherein $R^{1A}$ represents a lower alkyl group; $R^{2A}$ represents a formyl group; $R^{3A}$ represents a hydroxy group; or $R^{2A}$ and $R^{3A}$ taken together represent an oxo group; or $R^{3A}$ forms a double bond in combination with $R^{5A}$; $R^{4A}$ represents a lower alkyl group; $R^{5A}$ represents a hydrogen atom or a hydroxy(lower)alkyl group or forms a double bond in combination with $R^{3A}$ or $R^{6A}$; $R^{6A}$ represents a hydrogen atom or forms a double bond in combination with $R^{5A}$; $R^7$ represents a hydrogen atom or a lower alkyl group, provided that when $R^7$ is isopropyl then $R^{5A}$ is not hydroxymethyl;

Formula (9)

(9)

wherein $R^{1A}$, $R^{4A}$ and $R^7$ are as defined above; $R^{2a}$ represents a formyl group, a tri(lower)alkylsilyloxygroup, a trifluoromethylsulfonyloxy group or $$Ph_2PCH-, \underset{OR^{10}}{\overset{O}{\parallel}}$$

wherein $R^{10}$ represents a lower alkyl group and Ph represents a phenyl group; $R^{3a}$ represents a hydroxy group; or $R^{2a}$ and $R^{3a}$ taken together represent an oxo group or $R^{10}O$—CH═, where $R^{10}$ is as defined above; or $R^{3a}$ forms a double bond in combination with $R^{5a}$; $R^{5a}$ represents a hydrogen atom or a hydroxy(lower)alkyl group, or $R^{5a}$ forms a double bond in combination with $R^{3a}$ or $R^{6a}$; $R^6$ represents a hydrogen atom or forms a double bond in combination with $R^{5a}$; $R^8$ represents a hydrogen atom or a lower alkoxy group; $R^9$ represents a lower alkyl group; provided that when $R^7$ is isopropyl then $R^{5a}$ is not hydroxymethyl and provided that when $R^7$ and $R^8$ concurrently represent a hydrogen atom then $R^{5a}$ and $R^{6a}$ do not combine to form a double bond;

Formula (10)

(10)

wherein $R^{1B}$ represents a lower alkyl group;

Formula (11)

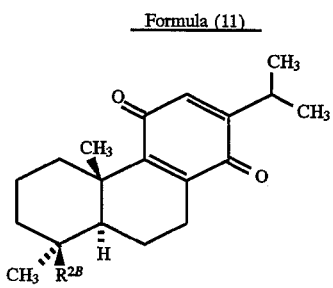

wherein $R^{2B}$ represents a hydroxymethyl group or a carboxyl group;

Formula (12)

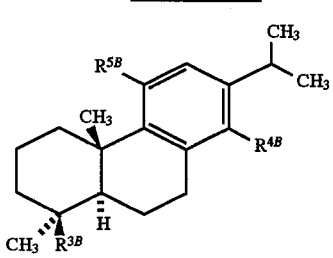

wherein $R^{3B}$ represents a lower alkoxycarbonyl group or a hydroxymethyl group; and $R^{4B}$ and $R^{5B}$ each represents a lower alkoxy group.

2. The method according to claim 1, wherein the phenanthrene derivative has a quinone or hydroquinone structure.

3. The method according to claim 1, wherein the phenanthrene derivative is represented by formula (1) or a salt thereof.

4. The method according to claims 1, wherein the phenanthrene derivative is represented by formula (4), wherein $R^3$ represents a hydrogen atom, or a salt thereof.

5. The method according to claim 1, wherein the phenanthrene derivative is represented by formula (11) or a salt thereof.

6. The method according to claim 1, wherein the phenanthrene derivative is represented by Compound 1, Compound 2, Compound 3, Compound 4, Compound 5 or Compound 6:

Compound 1

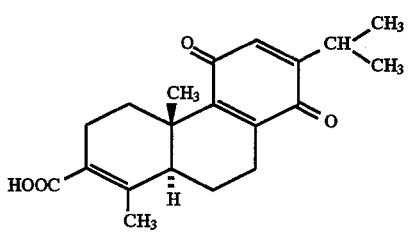

Compound 2

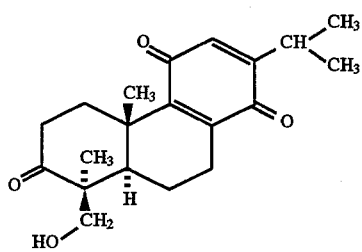

Compound 3

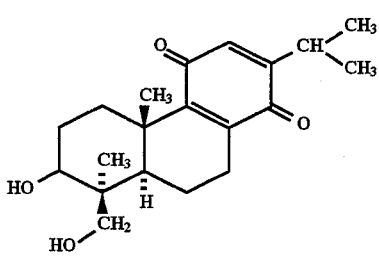

Compound 4

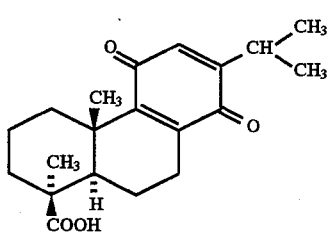

Compound 5

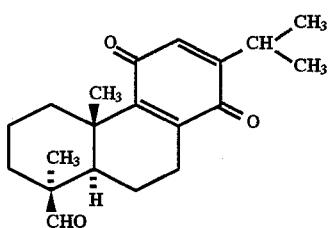

Compound 6

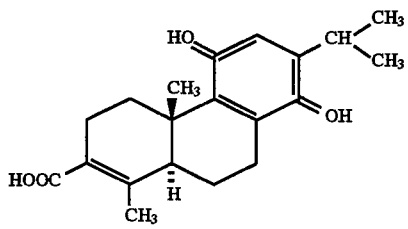

* * * * *